United States Patent [19]

Tokuda et al.

[11] Patent Number: 5,463,013
[45] Date of Patent: Oct. 31, 1995

[54] MODIFIED AROMATIC POLYCARBONATE RESIN, MODIFIED AROMATIC POLYESTER CARBONATE RESIN, MODIFIED POLYARYLATE, AND MOLDED ARTICLES THEREFROM

[75] Inventors: Toshimasa Tokuda, Iyo; Ikkoh Furukawa, Mihara; Masayoshi Miyauchi, Matsuyama, all of Japan

[73] Assignee: Teijin Chemicals, Ltd., Tokyo, Japan

[21] Appl. No.: 233,883

[22] Filed: Apr. 26, 1994

[30] Foreign Application Priority Data

Apr. 27, 1993 [JP] Japan ................. 5-101081
Apr. 27, 1993 [JP] Japan ................. 5-101083

[51] Int. Cl.$^6$ ..................... C08G 64/00
[52] U.S. Cl. .............. 528/196; 528/198; 524/601
[58] Field of Search ................. 528/196, 198; 524/601

[56] References Cited

U.S. PATENT DOCUMENTS 5,202,304  4/1993  Iwakura et al. ................. 503/209

*Primary Examiner*—James J. Seidleck
*Assistant Examiner*—Terressa Mosley
*Attorney, Agent, or Firm*—Sherman and Shalloway

[57] ABSTRACT

A modified aromatic polycarbonate resin containing at least one substituted phenyloxy group of the formula (I) in an amount of at least 5 mol % of the total amount of terminals,

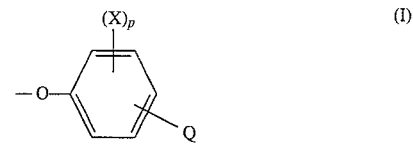

wherein:

X is a halogen atom or a monovalent aliphatic hydrocarbon group having 1 to 10 carbon atoms, p is an integer of 0 to 4, and

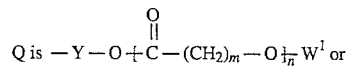
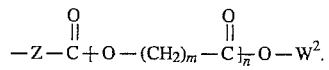

The present invention provide a modified aromatic polycarbonate resin of which the melt fluidity and electric properties are improved without impairing the excellent properties inherent to a polycarbonate resin such as transparency, heat resistance and dimensional stability.

25 Claims, 2 Drawing Sheets

MODIFIED AROMATIC POLYCARBONATE RESIN, MODIFIED AROMATIC POLYESTER CARBONATE RESIN, MODIFIED POLYARYLATE, AND MOLDED ARTICLES THEREFROM

DETAILED DESCRIPTION OF THE INVENTION

1. Industrial Field of the Invention

The present invention relates to a modified aromatic polycarbonate resin, a molded article thereof, a composition thereof, and a substituted phenol compound used for the modification of an aromatic polycarbonate resin. It also relates to a modified aromatic polyester carbonate resin and a modified polyarylate resin. In particular, it relates to a modified aromatic polycarbonate resin which retains the excellent transparency and mechanical properties of an aromatic polycarbonate resin and has improved melt fluidity and tracking resistance and a molded article thereof.

2. Prior Art of the Invention

As a typical aromatic polycarbonate resin, an aromatic polycarbonate resin obtained by reacting 2,2-bis(4-hydroxyphenyl)propane (generally called bisphenol A) with phosgene or a carbonate precursor such as diphenyl carbonate is known and mass-produced. This polycarbonate resin is widely used in a variety of fields since a molded article thereof has excellent properties such as excellence in transparency, heat resistance and dimensional accuracy. In recent years, the polycarbonate resin is also widely used as a substrate for information recording media in the field of an optical disk.

With a recent downsizing tendency of household utensils, home electric appliances, video units and their accessories and audio units and their accessories, it is now desired to develop an aromatic polycarbonate resin which is much more improved in melt fluidity and replicating properties. In the field of electric appliances, it is also demanded to develop an aromatic polycarbonate resin having improved tracking resistance.

For improving an aromatic polycarbonate resin in the melt fluidity, there is proposed a method in which the average molecular weight of the aromatic polycarbonate resin is decreased to the lowest level possible, a method in which a plasticizer is added, a method in which the polymer terminal is provided with a long-chain aliphatic hydrocarbon substituent or a method in which a polymer blend is formed. The defect with these methods is that the excellent properties inherent to an aromatic polycarbonate resin cannot be retained, that is, the physical properties are decreased or the transparency is impaired.

SUMMARY OF THE INVENTION

It is a first object of the present invention to provide a modified aromatic polycarbonate resin of which the melt fluidity is improved without substantially impairing the excellent properties inherent to a polycarbonate resin such as transparency, heat resistance and dimensional stability.

It is a second object of the present invention to provide a modified aromatic polycarbonate resin which has improved electric insulation properties, particularly improved tracking resistance, while it retains the excellent properties of a polycarbonate resin described above.

It is a third object of the present invention to provide a modified aromatic polycarbonate resin having excellent properties as a raw structural material for a variety of electric and electronic parts and optical parts, and a molded article thereof.

It is further another object of the present invention to provide a modified aromatic polyestercarbonate resin and a modified polyarylate resin of which the melt fluidity is improved with retaining the excellent properties inherent to an aromatic polycarbonate resin and a polyarylate resin, such as transparency and mechanical strength.

It is still further another object of the present invention to provide a substituted phenol compound used as a modifier for obtaining the above modified aromatic polycarbonate resin, an improved aromatic polyester carbonate resin and an improved polyarylate resin.

[I] Modified aromatic polycarbonate and method for the production thereof

According to the present invention, the above objects and advantages of the present invention are achieved, first, by a modified aromatic polycarbonate resin containing at least one substituted phenyloxy group of the formula (I) in an amount of at least 5 mol % of the total amount of terminals,

wherein:

X is a halogen atom or a monovalent aliphatic hydrocarbon group having 1 to 10 carbon atoms, p is an integer of 0 to 4, and

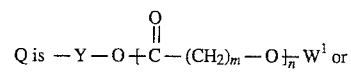

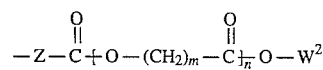

in which:

Y is a divalent aliphatic hydrocarbon group having 1 to 10 carbon atoms, $W^1$ is a hydrogen atom,

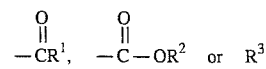

in which each of $R^1$, $R^2$ and $R^3$ is a monovalent aliphatic hydrocarbon group having 1 to 10 carbon atoms, a monovalent alicyclic hydrocarbon group having 4 to 8 carbon atoms or a monovalent aromatic hydrocarbon group having 6 to 15 carbon atoms, m is an integer of 4 to 20, n is an integer of 1 to 100, Z is a single bond or a divalent aliphatic hydrocarbon group having 1 to 10 carbon atoms, and $W^2$ is a hydrogen atom, a monovalent aliphatic hydrocarbon group having 1 to 10 carbon atoms, an alicyclic hydrocarbon group having 4 to 8 carbon atoms or a monovalent aromatic hydrocarbon group having 6 to 15 carbon atoms.

Most of known aromatic polycarbonate resins generally have terminals having a phenyloxy group or an alkyl-substituted phenyloxy group. These terminal groups contribute to the adjustment of the polymerization degree and the improvement of the polymer in heat resistance. In the present invention, the specifically structured, substituted phenyloxy group of the formula (1) is present in an amount of at least 5 mol %, preferably 7 to 90 mol %, of the total amount of terminals, whereby the melt fluidity and the processability are improved without impairing the excellent properties of an aromatic polycarbonate resin, such as transparency, heat resistance and dimensional stability, and moreover, the electric properties are improved.

The substituted phenyloxy group of the formula (1) has a characteristic feature in that the phenyloxy group has a structure in which the oxyalkylene ester group represented by Q or its polymer residue is substituted by the phenyloxy group.

The present invention will be detailed hereinafter.

In the aromatic polycarbonate resin, at least 5 mol % of the total terminals thereof is to be substituted with the substituted phenyloxy group of the formula (1) can be selected from known polycarbonate resins or industrially produced polycarbonate resins. That is, the skeleton of the aromatic polycarbonate resin of the present invention can be a polymer obtained by the reaction between a dihydric phenol and a carbonate precursor.

The dihydric phenol used for the production of the aromatic polycarbonate resin includes monocyclic and bicyclic dihydric phenols. Specific examples of the monocyclic dihydric phenol include hydroquinone and resorcinol. Specific examples of the bicyclic phenol include compounds of the formula (III),

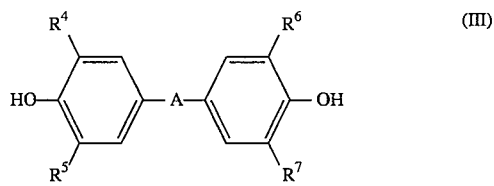

wherein each of $R^4$, $R^5$, $R^6$ and $R^7$ is independently a hydrogen atom, a halogen atom, an aliphatic hydrocarbon group having 1 to 6 carbon atoms or an aromatic hydrocarbon group having 6 to 12 carbon atoms, A is a single bond, —O—, —S—, —SO$_2$—, an alkylene group having 1 to 6 carbon atoms, an alkylidene group having 2 to 6 carbon atoms, a cycloalkylene group having 6 to 10 carbon atoms, a cycloalkylidene group having 6 to 10 carbon atoms or a phenyl-substituted alkylidene group having 2 to 6 carbon atoms.

Specific examples of the above dihydric phenols for forming the aromatic polycarbonate resin include hydroquinone, resorcin, 4,4'-dihydroxydiphenyl, bis(4-hydroxyphenyl)methane, 1,1-bis(4-hydroxyphenyl)ethane, 2,2-bis(4-hydroxyphenyl)propane (generally called bisphenol A), 2,2-bis(3-methyl-4-hydroxyphenyl)propane, 1,1-bis(4-hydroxyphenyl)cyclohexane, 2,2-bis(3-phenyl-4-hydroxyphenyl)propane, 2,2-bis(3-isopropyl-4-hydroxyphenyl)propane, 2,2-bis(4-hydroxyphenyl)butane, 2,2-bis(3,5-dimethyl-4-hydroxyphenyl)propane, 2,2-bis(3,5-dibromo-4-hydroxyphenyl)propane, 4,4'-dihydroxydiphenylsulfone, 4,4'-dihydroxydiphenylsulfoxide, 4,4'-dihydroxydiphenylsulfide, 3,3'-dimethyl-4,4'-dihydroxydiphenylsulfide, 4,4'-dihydroxydiphenyloxide, 9,9-bis(4-hydroxyphenyl)fluorene, 1,1-bis(4-hydroxyphenyl)-3,3,5-trimethylcyclohexane and 1,3-bis(4-hydroxyphenyl)-5,7-dimethyladamantane.

Of the above dihydric phenols, preferred are 2,2-bis(4-hydroxyphenyl)propane (bisphenol A), 2,2-bis(3-methyl-4-hydroxyphenyl)propane, 1,1-bis(4-hydroxyphenyl)cyclohexane, 2,2-bis(3-phenyl-4-hydroxyphenyl)propane, 2,2-bis(3-isopropyl-4-hydroxyphenyl)propane. 2,2-bis(4-hydroxyphenyl)butane, 9,9-bis(4-hydroxyphenyl)fluorene, 1,1-bis(4-hydroxyphenyl)-3,3,5-trimethylcyclohexane and 1,3-bis(4-hydroxyphenyl)-5,7-dimethyladamantane.

Further, in view of practical use and physical properties, more preferred are bisphenol A, 1,1-bis(4-hydroxyphenyl)cyclohexane, 9,9,-bis(4-hydroxyphenyl)fluorene, 1,1-bis(4-hydroxyphenyl)-3,3,5-trimethylcyclohexane and 1,3-bis(4-hydroxyphenyl)-5,7-dimethyladamantane. The above dihydric phenols may be used alone or in combination. Further, a small amount of a trifunctional compound may be used as a branching agent, and a small amount of an aliphatic difunctional compound may be used in combination. Above all, bisphenol A is preferred for the preparation of the aromatic polycarbonate resin of the invention.

A study of the present inventors has further revealed that the modified aromatic polycarbonate resin obtained by the modification of an aromatic polycarbonate resin obtained from 1,1-bis(4-hydroxyphenyl)-3,3,5-trimethylcyclohexane as a dihydric phenol is excellent in moldability and that a molded article from the modified aromatic polycarbonate resin is excellent in heat resistance, transparency and mechanical properties. Therefore, the above resin gives a molded article suitable for use in the optical field where heat resistance is required.

The aromatic polycarbonate resin can be produced by the reaction between the above dihydric phenol and a carbonate precursor. Examples of the carbonate precursor include phosgene, phosgene dimer, phosgene trimer and bischloroformates of the above dihydric phenols. Above all, phosgene is preferred.

The aromatic polycarbonate resin can be produced from the dihydric phenol and the carbonate precursor, for example, by a generally employed method in which the dihydric phenol is allowed to react with the carbonate precursor such as phosgene. The reaction between the dihydric phenol and phosgene is generally carried out in the presence of an acid scavenger and a solvent. The acid scavenger is selected, for example, from alkali metal hydroxides such as sodium hydroxide and potassium hydroxide and pyridine. The solvent is selected, for example, from halogenated hydrocarbons such as methylene chloride and chlorobenzene. Further, a catalyst may be used for the promotion of the reaction, and the catalyst is selected from tertiary amines and quaternary ammonium. The reaction temperature is generally between 0° and 40° C., and the reaction time is several minutes to 5 hours. During the reaction, preferably, the pH is generally maintained at least 10.

The modified aromatic polycarbonate resin of the present invention can be produced as follows. When the above aromatic polycarbonate resin is produced, a monofunctional phenol compound is allowed to be co-present together with the dihydric phenol compound and the carbonate precursor so that the substituted phenyloxy group of the formula (1) bonds to a terminal group.

That is, a typical compound used for the forming the terminal group of the formula (I) is a substituted phenol compound of the formula (II).

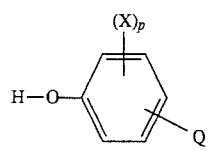

In the formula (II), X, P and Q are as defined in the formula (I).

The substituted phenol compound of the above formula (II) is a monofunctional compound having one phenolic hydroxyl group, and it works as a terminal-forming agent and bonds to a terminal group. For obtaining the modified aromatic polycarbonate resin of the present invention, other monofunctional phenol compound may be used in combination with the substituted phenol compound of the formula (II). The "other monofunctional phenol compound" has the following formula (IV).

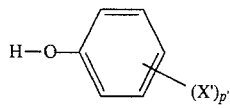

wherein X' is a halogen atom or an aliphatic hydrocarbon group having 1 to 10 carbon atoms, and p' is an integer of 0 to 5.

Specific examples of the monofunctional phenol compound of the formula (IV) include phenol, p-tert-butylphenol, p-cumylphenol and isooctylphenol.

When the modified aromatic polycarbonate resin of the present invention is produced, the amount of the substituted phenol compound of the formula (II), the amount of the monofunctional phenol compound of the formula (IV) and the proportions of these phenol compounds are determined on the basis of the kind of the polycarbonate resin, the kind of the terminal group, the polymerization degree and desired properties.

In the modified aromatic polycarbonate resin of the present invention, the substituted phenyloxy group of the formula (I) is present in an amount of at least 5 mol %, preferably 7 to 90 mol %, particularly preferably 10 to 80 mol %, of the total amount of terminal groups of the modified aromatic polycarbonate resin. The substituted phenyloxy group of the formula (I) is introduced into the terminal of the polymer owing to the use of the substituted phenol compound of the formula (II). The modified aromatic polycarbonate resin of the present invention contains the substituted phenyloxy group of the formula (I) in the above-specified amount, while the remaining terminals are not specially limited. However, the remaining terminals preferably have terminal groups derived from the monofunctional phenol compound of the formula (IV).

The easiest method for the production of the modified aromatic polycarbonate resin of the present invention is a method in which the substituted phenol compound of the formula (II) is added to raw material during the polymerization carried out for forming the aromatic polycarbonate resin.

The modified aromatic polycarbonate resin of the present invention may be also produced by another method in which the polycarbonate resin is synthesized and then a reactive compound is further added to the synthesized polycarbonate resin to obtain the modified polycarbonate resin containing the substituted phenyloxy group of the formula (I) as a terminal group.

Further, there is another method in which a reactive compound is added to the modified aromatic polycarbonate resin obtained by adding the compound of the formula (II) during the polymerization thereby to convert the terminal group to another terminal group which is included in the substituted phenyloxy group of the formula (I). As described above, there may be employed the above method in which the modified aromatic polycarbonate resin is once produced and then an intended terminal group is imparted by a post-treatment. (This method will be sometimes referred to as "post-treatment method" hereinafter).

In the above method, for example, the compound of the above formula (II) wherein $W^1$ is a hydrogen atom is used to obtain a modified aromatic polycarbonate resin having said compound as a terminal group, and then the terminal alcoholic hydroxyl group of the compound of the formula (II) is blocked in the form of a carboxylic ester

or a carbonate ester

This blocking can be carried out by reacting carboxylic acid chloride or chloroformate ester with the above modified aromatic polycarbonate resin. The carboxylic acid chloride used above has the formula of $ClCOR^1$ in which $R^1$ is a monovalent hydrocarbon group having 1 to 10, preferably 1 to 5, carbon atoms, an alicyclic hydrocarbon group having 4 to 8, preferably 5 to 6, carbon atoms or an aromatic hydrocarbon group having 6 to 15, preferably 6 to 12, carbon atoms as defined in the above formulae (I) and (II). The above chloroformate ester has the formula of $ClOCOOR^2$ in which $R^2$ is selected from those hydrocarbon groups specified concerning the above $R^1$.

When the molecular weight of the above-obtained modified aromatic polycarbonate resin is too small, the modified aromatic polycarbonate resin is fragile and cannot be practically used. When a solution of 0.7 g of the modified aromatic polycarbonate resin in 100 ml of methylene chloride is measured for a specific viscosity at 20° C. to show at least 0.165, the modified aromatic polycarbonate resin gives a molded article having excellent properties. The above specific viscosity is preferably 0.229 to 0.539, particularly preferably 0.264 to 0.451.

The modified aromatic polycarbonate resin of the present invention can be molded by any one of an injection molding method, a compression molding method, an extrusion molding method and a solution casting method. The modified aromatic polycarbonate resin of the present invention may contain additives such as a heat stabilizer, an antioxidant, a light stabilizer, a colorant, an antistatic agent, a lubricant and a mold release agent and inorganic fillers such as a glass fiber, glass beads, a carbon fiber, a metal fiber, talc and silica. Further, it may be used as a blend with other polycarbonate resin or other thermoplastic resin.

The modified aromatic polycarbonate resin according to the present invention has remarkably improved melt fluidity while it retains the excellent transparency, heat resistance and mechanical properties inherent to an aromatic polycarbonate resin. It can be also applied to a low-temperature high-cycle molding, and it has remarkably improved tracking resistance.

The modified aromatic polycarbonate resin of the present invention that has particularly excellent properties and the use thereof will be explained hereinafter.

In general, a molded article from the modified aromatic polycarbonate resin is excellent in transparency, and it is also excellent in optical properties.

When at least one of the following materials is used as the dihydric phenol for the production of the modified aromatic polycarbonate resin, a molded article from the modified aromatic polycarbonate resin is excellent in optical properties and particularly has a small birefringence. That is, the raw materials as the dihydric phenol are 2,2-bis(3-methyl-4-hydroxyphenyl)propane, 1,1-bis(3-methyl-4-hydroxyphenyl)cyclohexane, 1,1-bis(4-hydroxyphenyl)-1-phenylethane, 1,1-bis(3-methyl-4-hydroxyphenyl)-1-phenylethane, 2,2-bis(3-phenyl-4-hydroxyphenyl)propane, 4,4'-dihydroxytetraphenylethane, 2,2-bis(4-hydroxyphenyl)butane, 9,9-bis(4-hydroxyphenyl)fluorene, 1,1-bis(4-hydroxyphenyl)-3,3,5-trimethylcyclohexane, 2,2-bis(3-isopropyl-4-hydroxyphenyl)propane and 1,3-bis(4-hydroxyphenyl)-5,7-dimethyladamantane. Therefore, a molded article produced from the above modified aromatic polycarbonate resin in a flat form is applicable to the field where a low birefringence is required. A molded article from the above modified aromatic polycarbonate resin is hence suitable for use as a structural material or a functional material for an optical part such as a flat panel for a liquid crystal unit, an optical card, an optical disk, an optical fiber, an optical waveguide path, a connector, various lenses, a prism and a film.

Further, when 1,1-bis(4-hydroxyphenyl)-3,3,5-trimethylcyclohexane is used as the dihydric phenol, the modified aromatic polycarbonate resin is excellent over any other resin in heat resistance and a photoelasticity constant and can be preferably used for the production of a lens for a lamp. Further, the above modified aromatic polycarbonate resin can be also used for the production of a substrate for an optical recording medium.

For the use of the above modified aromatic polycarbonate resin for the production of a substrate for an optical recording medium, preferred is the modified aromatic polycarbonate of which the specific viscosity (a) and the following constant (b) satisfy the following expressions.

$$0.23 \leq \eta_{sp} \leq 0.37 \qquad (a)$$

$$30 \leq N \leq 60 \qquad (b)$$

wherein $\eta_{sp}$ is a specific viscosity of the modified aromatic polycarbonate resin and n is a proportion (%) of an ester unit

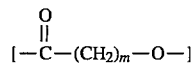

of the substituted phenyloxy group of the formula (I) based on the total molar amount of the dihydric phenol unit and the above ester unit in the modified aromatic polycarbonate resin.

Further, when the modified aromatic polycarbonate resin of the present invention is mixed with a filler of glass having a refractive index of which the difference from the refractive index of the modified aromatic polycarbonate resin is within a predetermined range, the mixture gives a resin composition having improved transparency and excellent properties.

According to the present invention, therefore, there is provided a resin composition comprising 40 to 95% by weight of the modified aromatic polycarbonate resin of the present invention and 60 to 5% by weight of a filler of glass having a refractive index of which the difference from that of the modified aromatic polycarbonate resin is 0.01 or less, and a molded article formed therefrom.

The refractive index difference between the modified aromatic polycarbonate resin and the above filler of glass is 0.01 or less, preferably 0.005 or less. When this difference exceeds 0.01, the transparency decreases. The filler of glass may have any one of the forms that can be generally applied to a thermoplastic resin such as a fiber, granules, flakes, plates. When the filler has the form of a fiber, preferably, the diameter is 3 to 25 μm and the fiber length in a molded article is approximately 0.02 to 0.5 mm. Further, the filler of glass may be surface-treated with a silane-coupling agent for increasing the affinity with the resin, and it may be also subjected to a binding treatment with an epoxy resin, an acrylic resin or a urethane resin for improving the handing properties. The amount of the filler of glass is 5 to 60% by weight, preferably 10 to 55% by weight. When this amount is less than 5% by weight, it is difficult to obtain a sufficient effect on the reinforcement with glass. When it is more than 60% by weight, undesirably, the moldability of the composition decreases.

The above resin composition can be produced by any method. For example, it can be produced by a method in which the modified aromatic polycarbonate resin and the filler of glass are dry-blended with a tumbler, a super mixer or Nauter mixer and then pelletized with an extruder, or a method in which the modified aromatic polycarbonate resin and other additive are mixed in advance and then the mixture and a glass fiber are co-extruded to pelletize them. The resin composition can be molded by any one of an injection molding method, a compression molding method and an extrusion molding method.

The above resin composition may contain a variety of other heat stabilizers and antioxidants as required. Examples of the heat stabilizers include triesters, diesters and monoesters of phosphorous acid such as triphenyl phosphite, trisnonylphenyl phosphite, tris(2,4-di-tert-butylphenyl)phosphite, tridecyl phosphite, trioctyl phosphite, trioctadecyl phosphite, didecylmonophenyl phosphite, dioctylmonophenyl phosphite, diisopropylmonophenyl phosphite, monobutyldiphenyl phosphite, monodecyldiphenyl phosphite, monooctyldiphenyl phosphite, bis(2,6-di-tert-butyl-4-methylphenyl)pentaerythritol diphosphite, 2,2-methylenebis(4,6-di-tert-butylphenyl)octyl phosphite, bis(nonylphenyl)pentaerythritol diphosphite, bis(2,4-di-tert-butylphenyl)pentaerythritol diphosphite and tetrakis(2,4-di-tert-butylphenyl)-4,4-diphenylene phosphonate. These heat stabilizers may be used alone or in combination. Examples of the antioxidants include phenol-containing antioxidants such as triethylene glycol-bis[3-(3-tert-butyl-5-methyl-4-hydroxyphenyl)propionate, 1,6-hdexanediol-bis[3-( 3,5-di-tert-butyl-4-hydroxyphenyl)propionate], pentaerythritol-tetrakis[3-(3,5-di-tert-butyl-4-hydroxyphenyl)propionate], octadecyl-3-(3,5-di-tert-butyl-4-hydroxyphenyl)propionate, 1,3,5-trimethyl-2,4,6-tris(3,5-di-tert-butyl-4-hydroxybenzyl)benzene, N,N-hexamethylenebis(3,5-di-tert-butyl-4-hydroxyhydrocinnamide), 3,5-di-tert-butyl-4-hydroxybenzylphosphonate-diethyl ester, tris(3,5-di-tert-butyl-4-hydroxybenzyl)isocyanurate and 3,9-bis{1,1-dimethyl-2-[β-(3-tert-butyl-4-hydroxy- 5-methylphenyl)propionyloxy]ethyl}-2,4,8,10-tetraoxaspiro( 5,5)undecane.

The amount of the above heat stabilizer and the antioxidant based on the modified aromatic polycarbonate resin is properly 0.00005 to 0.05% by weight. Further, the above resin composition may contain a higher fatty acid ester of a polyhydric alcohol. The fatty acid ester includes whole esters and partial esters of saturated aliphatic monocarboxylic acids having 8 to 22 carbon atoms with glycols, glycerol and pentaerythritol. The amount of the fatty acid ester is preferably approximately 0.001 to 0.2% by weight. The above resin composition may further contain additives such as a light stabilizer, a colorant, an antistatic agent and a lubricant. Further, the above resin composition may contain other polycarbonate resin and other thermoplastic resin.

The above resin composition containing a filler of glass has improved transparency, and hence can be remarkably suitably used for the production of molded articles in the fields of automotive parts, construction and electric and electronic parts.

[II] Substituted phenol compound and method for the production thereof:

The substituted phenol compound of the formula (II) used for the formation of a terminal group of the modified aromatic polycarbonate resin of the present invention and the method for the production thereof will be explained hereinafter.

The substituted phenol compound of the formula (II) is classified into a compound of the following formula (II-a) and a compound of the following formula (II-b) on the basis of its structures and synthesis methods.

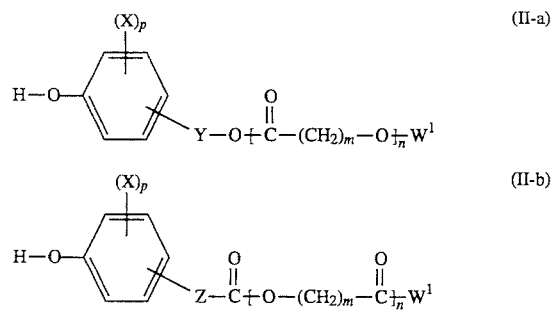

In the above formulae (II-a) and (II-b), X, p, Y, Z, $OW^2$, $W^2$, m and n have the following meanings.

X is a halogen atom or a monovalent hydrocarbon group having 1 to 10, preferably 1 to 5, carbon atoms.

p is an integer of 0 to 4.

Y is a divalent aliphatic hydrocarbon group having 1 to 10, preferably 1 to 5, carbon atoms.

$W^1$ is a hydrogen atom,

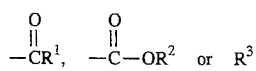

in which each of $R^1$, $R^2$ and $R^3$ is a monovalent aliphatic hydrocarbon group having 1 to 10, preferably 1 to 5, carbon atoms, a monovalent alicyclic hydrocarbon group having 4 to 8, preferably 5 to 6, carbon atoms or a monovalent aromatic hydrocarbon group having 6 to 15, preferably 6 to 12, carbon atoms.

m is an integer of 4 to 12, preferably 5 to 10.

n is an integer of 1 to 100, preferably 3 to 60, particularly preferably 4 to 50.

Z is a single bond or a divalent aliphatic hydrocarbon group having 1 to 10, preferably 1 to 5, carbon atoms.

$W^2$ is a hydrogen atom, a monovalent aliphatic hydrocarbon group having 1 to 10, preferably 1 to 5, carbon atoms, an alicyclic hydrocarbon group having 4 to 8, preferably 5 to 6, carbon atoms or a monovalent aromatic hydrocarbon group having 6 to 15, preferably 6 to 12, carbon atoms.

The substituted phenol compounds of the above formulae (II-a) and (II-b) may be produced by any methods, while they can be advantageously produced by the following methods.

The substituted phenol compound of the above formula (II-a) can be produced by a method in which a hydroxyaralkyl alcohol which has or does not have a substituent (X)

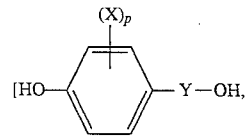

in which X, p and Y are as defined in the formula (II)] and a lactone

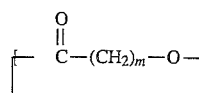

in which m is as defined in the formula (II)] are mixed in a proper mixing ratio and the mixture is heated in the presence of a catalyst. When the mixture is heated, the reaction between the alcoholic hydroxyl group of the hydroxyaralkyl alcohol and the lactone and the ring-opening polymerization of the lactone proceed at the same time. The polymerization degree [corresponding to n in the formula (II)] of the lactone can be adjusted as required by adjusting the molar ratio of the hydroxyaralkyl alcohol and lactone. When the polymerization degree of the lactone is too large, the reactivity of the phenolic hydroxyl group decreases. The polymerization degree (n) of the lactone is hence 100 or less, preferably 60 or less.

The above catalyst used for the production of the substituted phenol compound of the formula (II-a) is selected from organometallic compounds of metals such as lithium, sodium, potassium, aluminum, magnesium, beryllium, zinc, cadmium and boron and Lewis acids. The amount of the catalyst based on the total amount of the lactone is generally 0.001 to 10% by weight, preferably 0.01 to 3% by weight.

The reaction between the above substituted or nonsubstituted hydroxyaralkyl alcohol and lactone is carried out in an inert gas generally in a bulk form or in the presence of a solvent inert to the catalyst. The solvent is selected from benzene, toluene, xylene, ether, benzine, tetrahydrofuran and dioxane. The reaction temperature is generally 100° to 200° C., preferably 120° to 180° C., and the reaction is generally fully carried out for several minutes to several hours. After the reaction, the reaction mixture is purified by washing it with water when the solvent is used, and then the solvent is distilled off to obtain the product.

Specific examples of the hydroxyaralkyl alcohol include 2-hydroxybenzyl alcohol, 3-hydroxybenzyl alcohol, 4-hydroxybenzyl alcohol, 2-bromo-5-hydroxybenzyl alcohol, 3-chloro-4-hydroxybenzyl alcohol, 3-hydroxy-α-methylbenzyl alcohol, 4-hydroxy-α-methylbenzyl alcohol, 2-(2-hydroxyphenyl)ethanol, 2-(4-hydroxyphenyl)ethanol, 2-methyl-4-hydroxyphenylbenzyl alcohol, 2-methyl-6-hydroxyphenylbenzyl alcohol, 2-hydroxy-3-methylphenylbenzyl alcohol, 2-hydroxy-5-methylphenylbenzyl alcohol, 1-(4-hydroxyphenyl)-propanol-2, 3-(2-hydroxyphenyl)propanol, 3-(3-hydroxyphenyl)propanol, 2-hydroxy-5-ethylbenzyl alcohol, 3-methyl-4-hydroxyphenyl-α-methylbenzyl alcohol, 4-(2-hydroxyphenyl)butanol-2, 3-(2-hydroxy-5-methylphenyl)propanol, 5-(2-hydroxyphenyl)pentanol, 4-(2-methyl-4-hydroxyphenyl)butanol, 4-(3-methyl-4-hydroxyphenyl)butanol- 2, 3-(2-hydroxy-4-methylphenyl)butanol, 6-(4-hydroxyphenyl)hexanol-2 and 4-(4-hydroxyphenyl)hexanol-3. Of these, hydroxybenzyl alcohols are preferred.

The lactone has 5 to 21, preferably 6 to 11, carbon atoms, and a lower alkyl group may be substituted on carbon atoms forming the lactone ring. Specific examples of the lactone include δ-valerolactone, 7-hydroxyheptanoic acid lactone, 8-hydroxyoctanoic acid lactone, 13-hydroxytridecanoic acid lactone, 15-hydroxypentadecanoic acid lactone, 17-hydroxyheptadecanoic acid lactone, monomethyl-δ-valerolactone, monoethyl-δ-valerolactone, ε-caprolactone, monomethyl-ε-caprolactone and monoethyl-ε-caprolactone. δ-Valerolactone and ε-caprolactone are particularly preferred.

[III] Modified aromatic polyester carbonate resin and method for the production thereof According to the present invention, further, there is provided a modified aromatic polyester carbonate resin containing at least one substituted phenyloxy group of the formula (I) in an amount of at least 5 mol % of the total amount of terminals,

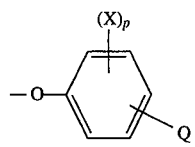

wherein X, p and Q are as defined above.

The above modified aromatic polyester carbonate resin of the present invention can be obtained by adding a substituted phenol compound of the above formula (II) to raw materials in the ordinary production of an aromatic polyester carbonate resin.

In the modified aromatic polyester carbonate resin of the present invention, the amount of the substituted phenyloxy group of the formula (I) based on the total amount of terminals is at least 5 mol %, preferably 7 to 90 mol %.

The terminals other than the substituted phenyloxy group of the formula (I) are not specially limited, while the remaining terminals may be residues derived from the monofunctional phenol compound of the above formula (IV).

Concerning the amount ratio of the ester bond and carbonate bond which constitute the modified aromatic polyester carbonate resin, the ester bond:carbonate bond ratio (molar ratio) is 5:95 to 75:25, preferably 10:90 to 50:50. Further, for retaining the properties of a molded article, the specific viscosity of the modified aromatic polyester carbonate resin is 0.229 to 0.539, preferably 0.246 to 0.451.

The modified aromatic polyester carbonate resin of the present invention can be produced by a method in which a dihydric phenol, one of an aromatic dicarboxylic acid and an ester-forming derivative thereof, and a carbonate precursor are allowed to react. Specifically, the modified aromatic polyester carbonate resin can be produced by a method in which phosgene is reacted with a dihydric phenol and one of an aromatic dicarboxylic acid and an acid chloride thereof or a method in which diphenyl carbonate is reacted with a dihydric phenol and one of an aromatic dicarboxylic acid and an ester thereof.

The reaction of the dihydric phenol, one of an aromatic dicarboxylic acid and an acid chloride thereof and phosgene is generally carried out in the presence of an acid scavenger and a solvent. The acid scavenger is selected, for example, from alkali metal hydroxides such as sodium hydroxide and potassium hydroxide and pyridine. The solvent is selected, for example, from halogenated hydrocarbons such as methylene chloride and chlorobenzene. For the promotion of the reaction, a catalyst such as a tertiary amine or quaternary ammonium salt may be used. The reaction temperature is generally between 0° and 40° C., the reaction time is several minutes to five hours, and the pH during the reaction is generally preferably maintained at at least 10. In particular, in the method using a dicarboxylic acid in which an ester carbonate anhydride is formed as an intermediate, the pH is adjusted to 7 to 9 in the reaction in which this ester carbonate anhydride is formed, and the pH is adjusted to 8 to 10 in the reaction in which the ester carbonate anhydride is decarboxylated.

In the method (ester exchange method) in which a dihydric alcohol, one of an aromatic dicarboxylic acid and an ester thereof and diphenyl carbonate are allowed to react, these components are mixed in an inert gas atmosphere and then allowed to react under reduced pressure generally at a temperature between 120° and 350° C. The vacuum degree is increased stepwise, and finally decreased to 1 mmHg or less to remove phenols formed out of the reaction system. The reaction time is generally approximately 1 to 4 hours. A catalyst and an antioxidant may be added as required.

During the polymerization for the synthesis of the above aromatic polyester carbonate resin, a predetermined amount of the above Substituted phenol compound of the formula (II) can be added.

The above dihydric phenol used for the production of the modified aromatic polyester carbonate resin can be selected from those dihydric phenols described with regard to the modified aromatic polycarbonate resin and the process for the production thereof, and those dihydric phenols which were described as preferred ones are also preferred in this case.

Examples of the aromatic dicarboxylic acid used for the production of the modified aromatic polyester carbonate resin include terephthalic acid, isophthalic acid, 5-tert-butylisophthalic acid, 4,4'-diphenyl ether dicarboxylic acid, 4,4'-benzophenonedicarboxylic acid, 4,4'-diphenylsulfonedicarboxylic acid, 2,2-bis(4-carboxylphenyl)propane, naphthalenedicarboxylic acid and trimethyl-3-phenylindane-4,5-dicarboxylic acid. Of these, terephthalic acid and isophthalic acid are particularly preferred. Examples of the ester-forming derivatives of these dicarboxylic acid includes acid chlorides and alkyl esters.

Examples of the carbonate precursor include phosgene, phosgene dimer, phosgene trimer, diphenyl carbonate, bis-chloroformates of the above dihydric phenols, di-p-tolylcarbonate, phenyl-p-tolylcarbonate, di-p-chlorophenylcarbonate and dinaphthylcarbonate. Of these, phosgene and diphenylcarbonate are preferred.

The modified aromatic polyester carbonate resin of the present invention can be molded by any one of an injection molding method, a compression molding method, an extrusion molding method and a solution casting method. The modified aromatic polyester carbonate resin of the present invention may contain additives such as a heat stabilizer, an antioxidant, a light stabilizer, a colorant, an antistatic agent, a lubricant and a mold release agent and inorganic fillers such as a glass fiber, glass beads, a carbon fiber, a metal fiber, talc and silica. Further, it may be used as a blend with other thermoplastic resins such as an aromatic polycarbonate resin.

The modified aromatic polyester carbonate resin according to the present invention has remarkably improved melt fluidity while it retains its the excellent transparency, heat resistance and mechanical properties. It is very useful in the fields of structural materials and functional materials for electric and electronic parts and optical parts such as an optical disk, an optical lens, a liquid crystal panel, an optical card, sheet, film an optical fiber, a connector, a vapor-deposited reflection mirror, a display and an OPC binder.

[IV] Modified polyarylate resin and method for the production thereof:

According to the present invention, there is provided a modified polyarylate resin containing at least one substituted phenyloxy group of the formula (I) in an amount of at least 5 mol % of the total amount of terminals,

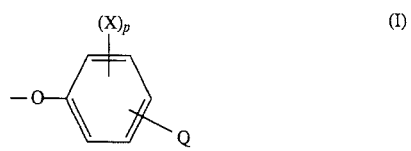

wherein X, p and Q are as defined above.

The above modified polyarylate resin of the present invention can be obtained by adding a substituted phenol compound of the above formula (II) to raw materials in the ordinary production of a polyarylate resin.

In the modified polyarylate resin of the present invention, the amount of the substituted phenyloxy group of the formula (I) based on the total amount of terminals is at least 5 mol %, preferably 7 to 90 mol %.

The terminals other than the substituted phenyloxy group of the formula (I) are not specially limited, while the remaining terminals may be residues derived from the monofunctional phenol compound of the above formula (IV).

The modified polyarylate resin of the present invention can be obtained by a method in which the substituted phenol compound of the above formula (II) is added to the raw materials in the production thereof. Further, it can be also produced by a method used for general polyarylate resins. That is, it can be obtained by allowing the dihydric phenol and an aromatic dicarboxylic acid chloride to react. This reaction for the production of the polyarylate resin is generally carried out in the presence of an acid scavenger and a solvent. The acid scavenger is selected, for example, from alkali metal hydroxides such as sodium hydroxide and potassium hydroxide and pyridine. The solvent is selected, for example, from halogenated hydrocarbons such as methylene chloride and chlorobenzene. Further, a catalyst may be used for the promotion of the reaction, and the catalyst is selected from tertiary amines and quaternary ammonium. The reaction temperature is generally between 0° and 40° C., and the reaction time is several minutes to 5 hours. During the reaction, preferably, the pH is generally maintained at least 10.

The above dihydric phenol used for the production of the modified polyarylate resin can be selected from those dihydric phenols described with regard to the modified aromatic polycarbonate resin and the process for the production thereof, and those dihydric phenols which were described as preferred ones are also preferred in this case.

Examples of the aromatic dicarboxylic acid dichloride used for the production of the modified polyarylate resin include dichlorides of terephthalic acid, isophthalic acid, 5-tert-butylisophthalic acid, 3,4-benzophenonedicarboxylic acid, 4,4'-diphenyl ether dicarboxylic acid, 3,3'-diphenyldicarboxylic acid, 4,4'-diphenyldicarboxylic acid, 2,2-bis(4-carboxylphenyl)propane, naphthalenedicarboxylic acid and trimethyl-3-phenylindane-4,5-dicarboxylic acid. Of these, dichlorides of terephthalic acid and isophthalic acid are particularly preferred.

The modified polyarylate resin can be obtained by the polymerization of the above dihydric phenol, the aromatic dicarboxylic acid dichloride and a predetermined amount of the substituted phenol compound of the formula (II). In this case, the monofunctional phenol compound of the formula (IV) may be added. Further, the same post treatment as that described with regard to the modified aromatic polycarbonate resin can be carried out to obtain the modified polyarylate having the intended terminal group.

The modified polyarylate resin of the present invention can be molded by any one of an injection molding method, a compression molding method, an extrusion molding method and a solution casting method. The modified aromatic polyester carbonate resin of the present invention may contain additives such as a heat stabilizer, an antioxidant, a light stabilizer, a colorant, an antistatic agent, a lubricant and a mold release agent and inorganic fillers such as a glass fiber, glass beads, a carbon fiber, a metal fiber, talc and silica. Further, it may be used as a blend with other thermoplastic resin such as a polycarbonate resin.

The modified polyarylate resin according to the present invention has remarkably improved melt fluidity while it retains its excellent transparency, heat resistance and mechanical properties. It is very useful in the fields of structural materials and functional materials for electric and electronic parts and optical parts such as an optical disk, an optical lens, a liquid crystal panel, an optical card, sheet, film, an optical fiber, a connector, a vapor-deposited reflection mirror, a display and an OPC binder.

[IV] Low-polymerization degree modified aromatic polycarbonate resin and use thereof:

According to the present invention, further, there is provided an aromatic polycarbonate resin having a low polymerization degree, having a specific viscosity of less than 0.165 and containing at least one substituted phenyloxy group of the formula (I) in an amount of at least 5 mol % of the total amount of terminals,

wherein X, p and q are as defined above.

The above aromatic polycarbonate resin having a low polymerization degree (to be abbreviated as "low polymer" hereinafter) has no morphological retainability per se and cannot be used as a raw material for a molded article. However, it can be used as a modifier for improving the melt fluidity of a thermoplastic resin, particularly an engineering plastic. In particular, the low polymer has an effect on the improvement of an aromatic polycarbonate resin in melt fluidity when incorporated in a predetermined amount. The low polymer properly has a specific viscosity of 0.105 to 0.164. The amount of the substituted phenyloxy group of the formula (I) in the low polymer is at least 5 mol %, preferably 7 to 90 mol %, of the total amount of terminals. The remaining terminals other than the substituted phenyloxy group of the formula (I) are not specially limited. However, the remaining terminals can have terminal groups derived from the monofunctional phenol compound of the formula (IV).

In principle, the above low polymer can be produced from the same raw materials by the same method as those explained with regard to the production of the modified aromatic polycarbonate resin. For preventing the increase of the polymerization degree, the reaction conditions and the amount of the monofunctional phenol compound [including the substituted phenol compound of the formula (II)] can be properly selected.

The above low polymer can be blended with thermoplastic engineering plastics having poor moldability such as polycarbonate, polysulfone and polyarylate, and the blend can be molded by any one of an injection molding method, a compression molding method, an extrusion method and a solution casting method. When the low polymer is used as a composition of the low polymer and a thermoplastic resin, the composition may further contain adding additives such as a heat stabilizer, an antioxidant, a light stabilizer, a colorant, an antistatic agent, a lubricant and a mold release agent and inorganic fillers such as a glass fiber, glass beads, a carbon fiber, a metal fiber, talc and silica.

EXAMPLES

The present invention will be explained more in detail hereinafter with reference to Examples, in which "part" stands for "part by weight" and "%" stands for "% by weight".

The properties described in Examples were evaluated as follows.

(a) Specific viscosity 0.7 Gram of a polymer sample was dissolved in 100 ml of methylene chloride and measured at 20° C.

(b) Glass transition temperature

Measured with a du Pont DSC 910.

(c) Total light transmittance

Measured with Sigma 80 supplied by Nippon Denshoku K.K.

(d) Melt fluidity (MFR)

Measured with a semi-automatic melt indexer supplied by Toyo Seiki K.K. according to JIS K7210.

(e) Izod impact strength

A sample (thickness ⅛ inch, notched) was measured according to JIS-K 7110.

(f) Tracking resistance

Measured according to IEC 112.

(g) Refractive index and Abbe's number

Measured with an Abbe refractometer supplied by Atago K.K. using α-bromonaphthalene as a contact liquid.

(h) Photoelasticity constant

Measured with a photoelasticity measuring apparatus supplied by Riken Keiki K.K.

(i) Fog value

Measured with Sigma 80 supplied by Nippon Denshoku K.K.

(j) Birefringence

Measured with an automatic birefringence measuring apparatus ADR-200B supplied by Oak Seisakusho for retardations at a wavelength of 632.8 nm in places 10, 20, 30, 40, 50, 60, 70, 80 and 90 cm apart from the end of a sheet sample while He-Ne laser was used as a light source.

(k) Warpage ratio

A maximum warpage per a length of 1,000 mm was expressed as a percentage according to JIS K-6911. The larger the value is, the greater the warpage is.

EXAMPLE 1 (SYNTHESIS OF SUBSTITUTED PHENOL COMPOUND)

Example 1-(i)

Figure 1:
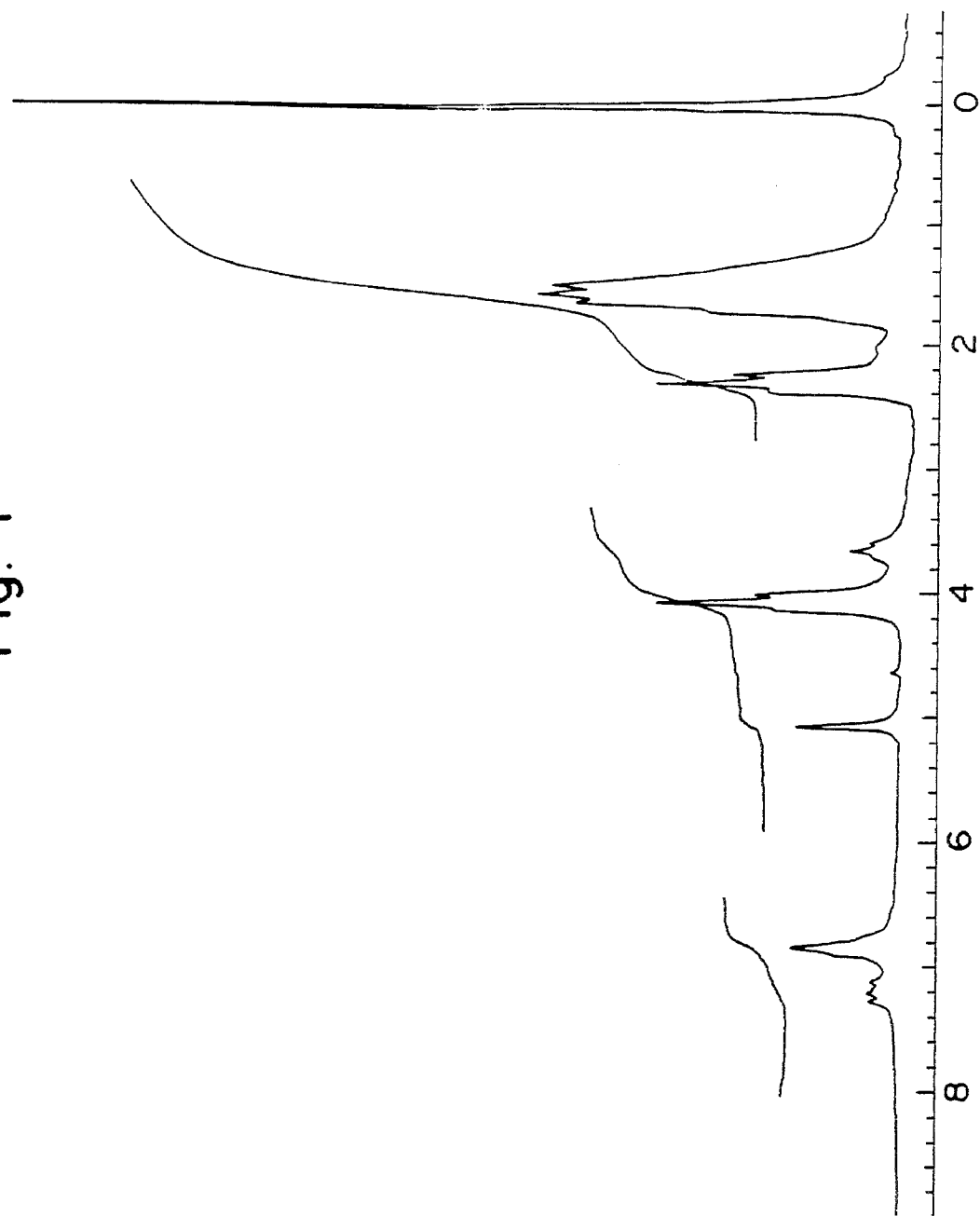
FIG. 1 is the NMR analysis chart of a substituted phenol compound obtained in Example 1.

248 Parts of m-hydroxybenzyl alcohol and 0.02 part of tetraisopropyl titanate were charged into a dry reactor having a thermometer, a stirrer and a reflux condenser, and heated to 145° C. in nitrogen current. At this temperature, 1,140 parts of ε-caprolactone containing 0.08 part of tetraisopropyl titanate was added over 70 minutes. During this addition, the temperature was gradually increased up to 180° C. Further, the reaction mixture was continuously stirred at 170° C. for 120 minutes to finish the reaction. The resultant reaction product had a hydroxyl value of 75.8 mg KOH/g and an acid value of 2.3 mg KOH/g. The yield thereof was almost quantitative. FIG. 1 shows the NMR chart of this reaction product. This NMR chart shows that the reaction product was a poly-ε-caprolactone terminated with phenol (n=5 on average). This reaction product is abbreviated as "substituted phenol compound A" hereinafter. That is, this reaction product had the following structure.

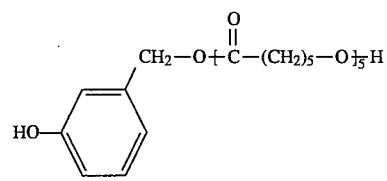

The above acid value and hydroxyl value of the above reaction product was measured according to the Japanese Pharmacopoeia oil and fats test method, and the NMR measurement used a perchloroform solution.

Example 1-(ii)

Figure 2:
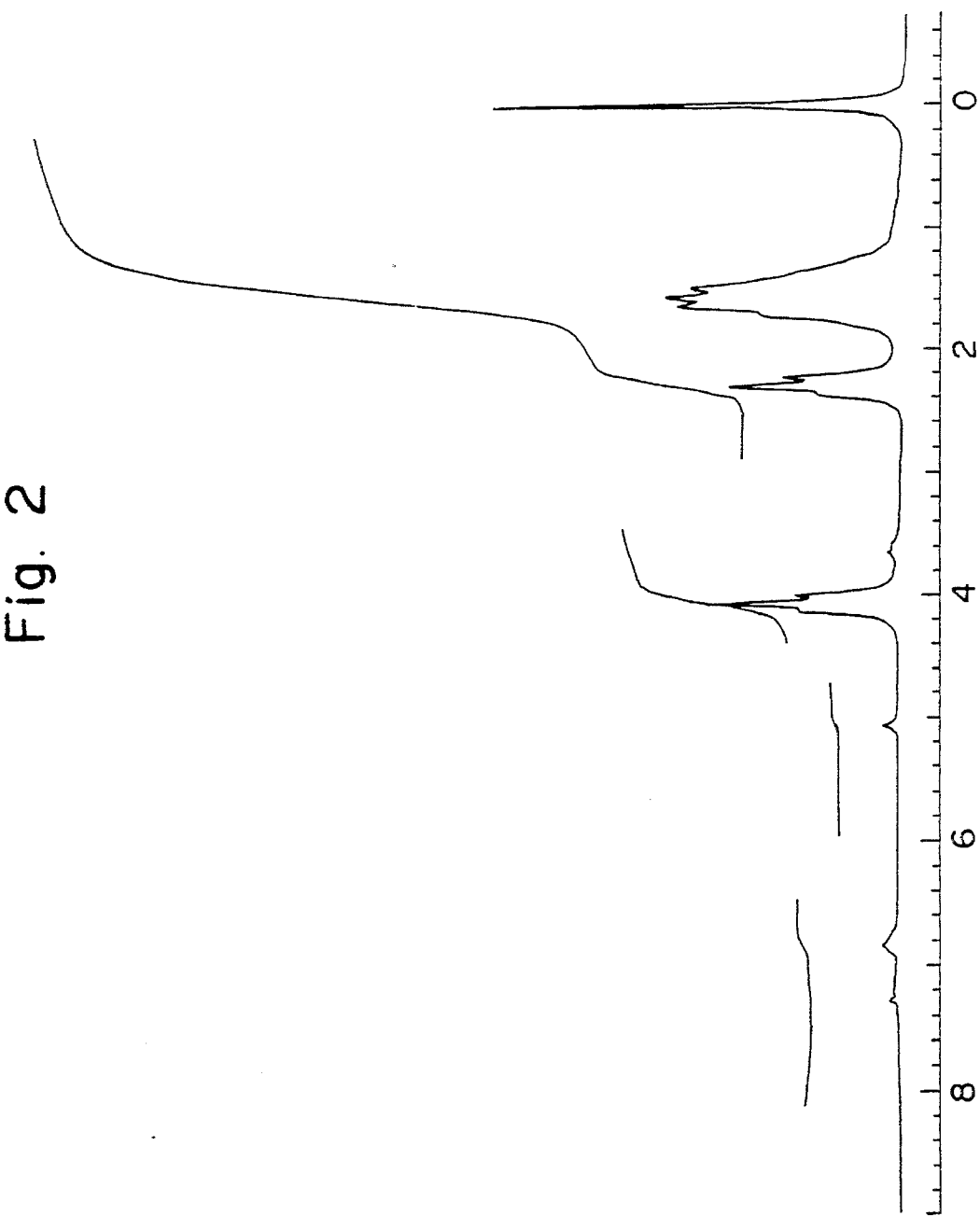
FIG. 2 is the NMR analysis chart of a substituted phenol compound obtained in Example 2.

Example 1-(i) was repeated except that the amount of m-hydroxybenzyl alcohol was changed to 62 parts. The resultant reaction product had a hydroxyl value of 24.3 mg KOH/g and an acid value of 1.0 mg KOH/g. The yield thereof was almost quantitative. FIG. 2 shows the NMR chart of this reaction product. This NMR chart shows that the reaction product was a poly-ε-caprolactone terminated with phenol (n=20 on average). This reaction product is abbreviated as "substituted phenol compound B" hereinafter.

Example 1-(iii)

Example 1-(i) was repeated except that the amount of m-hydroxybenzyl alcohol was changed to 68.9 parts. The resultant reaction product had a hydroxyl value of 26 mg KOH/g and an acid value of 1.5 mg KOH/g. The yield thereof was almost quantitative. The NMR chart thereof showed that the reaction product was a poly-ε-caprolactone terminated with phenol (n=18 on average). This reaction product is abbreviated as "substituted phenol compound C" hereinafter.

Example 1-(iv)

Example 1-(i) was repeated except that the amount of m-hydroxybenzyl alcohol was changed to 82.7 parts. The resultant reaction product had a hydroxyl value of 30 mg KOH/g and an acid value of 1.2 mg KOH/g. The yield thereof was almost quantitative. The NMR chart thereof showed that the reaction product was a poly-ε-caprolactone terminated with phenol (n=15 on average). This reaction product is abbreviated as "substituted phenol compound D" hereinafter.

EXAMPLE 2 (SYNTHESIS OF SUBSTITUTED PHENOL COMPOUND)

A flask was charged with 74.65 parts of methyl p-hydroxyphenylacetate, 1,02:5.3 parts of ε-caprolactone and 5.2 parts of diethylene glycol. Then, tetrabutoxytitanium was added to the reaction mixture such that the amount of the tetrabutoxytitanium was 10 ppm. In a nitrogen current, the reaction temperature was increased up to 220° C., and the mixture was allowed to react for 10 hours. Then, the reaction mixture was cooled, and analyzed by NMR and IR.

The analyses showed that the above reaction product had the following structure. This reaction product was abbreviated as "substituted phenol compound E" hereinafter.

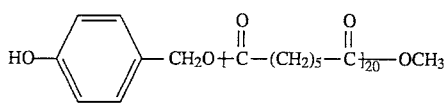

EXAMPLE 3

A reaction vessel having a thermometer, a stirrer, a phosgene-introducing tube and a reflux condenser was charged with 4,954 parts of ion-exchanged water and 347.7 parts of a 48% sodium hydroxide aqueous solution, and 955.9 parts of bisphenol A and 0.95 parts of hydrosulfite were dissolved in the charged mixture. Then, 3,049.5 parts of methylene chloride was added, and while the mixture was stirred, 456.8 parts of phosgene was blown into the mixture at 15° to 20° C. over 60 minutes. After the introduction of the phosgene was finished, a solution of 165.8 parts of the substituted phenol compound A in 400 parts of methylene chloride was added, and 174.9 parts of a 48% sodium hydroxide aqueous solution and 93.8 parts of bisphenol A were added to emulsify the reaction mixture. Then, 3 parts of trimethylamine was added, and the mixture was stirred at 28° to 33° C. for about 2 hours to finish the reaction. The reaction product was diluted with methylene chloride, washed with water, acidified with hydrochloric acid and then washed with water. When the electric conductivity of the aqueous phase was almost equivalent to that of ion-exchanged water, methylene chloride was evaporated to give 1,130 parts of a colorless modified polycarbonate (yield 92%). This polymer had a substituted phenol compound A content, when analyzed by IR absorption spectrum, of 12.3%, a specific viscosity of 0.390 a glass transition temperature of 104° C., an MFR of 28 g/10 minutes, a total light transmittance of 89% and an Izod impact strength of 41 kg.cm/cm.

EXAMPLE 4

The same reaction vessel as that used in Example 3 was charged with 4,206 parts of ion-exchanged water and 295.2 parts of a 48% sodium hydroxide aqueous solution, and 811.7 parts of bisphenol A and 2.4 parts of hydrosulfite were dissolved in the charged mixture. Then, 2,589.4 parts of methylene chloride was added, and 387.5 parts of phosgene was blown into the mixture under the same conditions as those in Example 3. After the introduction of the phosgene was finished, a solution of 487.8 parts of the substituted phenol compound B obtained in Example 1-(ii) in 800 parts of methylene chloride was added, and 148.5 parts of a 48% sodium hydroxide aqueous solution and 79.2 parts of bisphenol A were added. Thereafter, the procedures in Example 3 were repeated to give 1,321 parts of a modified polycarbonate (yield 95%). This polymer had a substituted phenol compound B content, when analyzed by IR absorption spectrum, of 34.3%, a specific viscosity of 0.355 and a glass transition temperature of 35.4C. This polymer was dry-blended with 20% of glass fiber chopped strands (3 PE-455 FB, supplied by Nitto Boseki Co., Ltd.) and the blend was extruded in the form of pellets. The pellets were injection-molded to prepare a plate having a thickness of 3 mm. The plate showed a tracking resistance, at 200 V, of at least 100 drops.

EXAMPLE 5

100 Parts of a polycarbonate from bisphenol A, having a specific viscosity of 0.405 [Panlite (tradename) L-1225W, supplied by Teijin Chemicals Limited] was mixed with 68.5 parts of the modified polycarbonate obtained in Example 3, and the mixture was extruded with an extruder at 250° C. to prepare pellets. These pellets had a substituted phenol compound A content, when analyzed by IR absorption spectrum, of 5%, an MFR of 17 g/10 minutes, a total light transmittance of 89% and an Izod impact strength of 86 kg.cm/cm.

EXAMPLE 6

100 Parts of a polycarbonate from bisphenol A, having a specific viscosity of 0.405 (Panlite L-225W, supplied by Teijin-Chemicals Limited) was mixed with 17.1 parts of the modified polycarbonate obtained in Example 4, and the mixture was extruded with an extruder at 250° C. to prepare pellets. These pellets had a substituted phenol compound B content, when analyzed by IN absorption spectrum, of 5%, an MFR of 18 g/10 minutes, a total light transmittance of 89% and an Izod impact strength of 85 kg.cm/cm.

EXAMPLE 7

100 Parts of a polycarbonate from bisphenol A, having a specific viscosity of 0.405 (Panlite L-1225W, supplied by Teijin Chemicals Limited) was mixed with 41.2 parts of the modified polycarbonate obtained in Example 4, and the mixture was extruded with an extruder at 230° C. to prepare pellets. These pellets had a substituted phenol compound B content, when analyzed by IR absorption spectrum, of 10%, an MFR of 25 g/10 minutes, a total light transmittance of 89% and an Izod impact strength of 45 kg.cm/cm.

COMPARATIVE EXAMPLE 1

100 Parts of a polycarbonate from bisphenol A, having a specific viscosity of 0.405 (Panlite L-1225W, supplied by Teijin Chemicals Limited) was extruded with an extruder at 270° C. to prepare pellets. These pellets had an MFR of 11 g/10 minutes, a total light transmittance of 90% and an Izod impact strength of 95 kg-cm/cm. This polymer was dry-blended with 20% of glass fiber chopped strands in the same manner as in Example 4, and evaluated for a tracking resistance to show a wide variability, as wide as 40 to 90 drops at 200 V.

COMPARATIVE EXAMPLE 2

100 Parts of a polycarbonate from bisphenol A, having a specific viscosity of 0.405 (Panlite L-1225W, supplied by Teijin Chemicals Limited), was dry-blended with 5% of a commercially available polycaprolactone (PLACCEL H-1, a number average molecular weight 10,000, supplied by Daicel Chemical Industries, Ltd.) and the mixture was extruded with an extruder at 260° C. to prepare pellets. These pellets had an apparent viscosity-average molecular weight of 22,000, a specific viscosity of 0.400, an MFR of 13 g/10 minutes, a total light transmittance of 88% and an Izod impact strength of 9 kg.cm/cm.

EXAMPLE 8

The same reaction vessel as that used in Example 3 was charged with 17,800 parts of ion-exchanged water and 3,732 parts of a 48.5% sodium hydroxide aqueous solution, and 3,131 parts of 1,1-bis(4-hydroxyphenyl)-3,3,5-trimethylcyclohexane was dissolved in the mixture. Then, 11,110 parts of methylene chloride was added, and while the mixture was stirred, 1,200 parts of phosgene was blown into the mixture at 20° C. over about 40 minutes. After the introduction of the phosgene was finished, the temperature inside the reaction vessel was increased up to 30° C., and 420.6 parts of the substituted phenol compound A was added to emulsify the reaction mixture. Then, 3.5 parts of triethylamine was added, and the mixture was stirred for about 2 hours and the reaction was finished. After the reaction, an organic phase was separated, diluted with methylene chloride, washed with water and then neutralized with hydrochloric acid. The resultant reaction product was repeatedly washed with water, and when the electric conductivity of the aqueous phase was almost equivalent to that of ion-exchanged water, an organic phase was separated and pulverized while methylene chloride was evaporated to give 3,794 parts of a colorless modified polycarbonate (yield 99.5%). This polymer had a specific viscosity of 0.339, a glass transition temperature of 175° C. and an MFR of 2.0 g/10 minutes. Then, 0.03% of tris(nonylphenyl)phosphite, 0.05% of Irganox 1076 and 0.2% of stearic acid monoglyceride were added to the above polymer, and the mixture was3melt-extruded at 280° C. to prepare pellets. The pellets were injection-molded to prepare a test piece (disk plate) having a diameter of 40 mm and a thickness of 1 mm. This test piece had a total light transmittance of 89%.

EXAMPLE 9

3,721 Parts (yield 99%) of a modified polycarbonate was obtained in the same manner as in Example 8 except that the amount of the substituted phenol compound A was changed to 350.5 parts and that 15.2 parts of p-tert-butylphenol was further used. This polymer had a specific viscosity of 0.293, a glass transition temperature of 176° C. and an MFR of 2.5 g/10 minutes. The same additives as those used in Example 8 were added to the polymer, and the resultant composition was molded and evaluated in the same manner as in Example 8 to show a total light transmittance of 89%.

EXAMPLE 10

3,736 Parts (yield 99%) of a modified polycarbonate was obtained in the same manner as in Example 8 except that the amount of the substituted phenol compound A was changed to 350.5 parts and that 30.3 parts of p-tert-butylphenol was further used. This polymer had a specific viscosity of 0.253, a glass transition temperature of 173° C. and an MFR of 4.0 g/10 minutes. The same additives as those used in Example 8 were added to the polymer, and the resultant composition was molded and evaluated in the same manner as in Example 8 to show a total light transmittance of 90%.

EXAMPLE 11

3,593 Parts (yield 98.5%) of a modified polycarbonate was obtained in the same manner as in Example 8 except that the amount of the substituted phenol compound A was changed to 210.3 parts and that 45.5 parts of p-tert-butylphenol was further used. This polymer had a specific viscosity of 0.290, a glass transition temperature of 180° C. and an MFR of 2.0 g/10 minutes. The same additives as those used in Example 8 were added to the polymer, and the resultant composition was molded and evaluated in the same manner as in Example 8 to show a total light transmittance of 90%.

COMPARATIVE EXAMPLE 3

3,469 Parts (yield 99.6%) of a polymer was obtained in the same manner as in Example 8 except that the substituted phenol compound A was replaced with 90.9 parts of p-tert-butylphenol was further used. This polymer had a specific viscosity of 0.248, a glass transition temperature of 227° C. and an MFR of 0.3 g/10 minutes. The same additives as those used in Example 8 were added to the polymer, and the resultant composition was molded and evaluated in the same manner as in Example 8 to show that the resultant molded article had a burn mark and had a low total light transmittance, as low as 83%.

EXAMPLE 12

The same reaction vessel as that used in Example 3 was charged with 4,954 parts of ion-exchanged water and 347.7 parts of a 48.5% sodium hydroxide aqueous solution, and 955.9 parts of bisphenol A and 0.95 parts of hydrosulfite were dissolved in the mixture. Then, 3,049.5 parts of methylene chloride was added, and while the mixture was stirred, 456.3 parts of phosgene was blown into the mixture at 15° to 20° C. over about 60 minutes. After the introduction of the phosgene was finished, a solution of 165.8 parts of the substituted phenol compound A in 400 parts of methylene chloride was added, and further, 174.9 parts of a 48% sodium hydroxide aqueous solution and 93.3 parts of bisphenol A were added to the mixture to emulsify it. Then, 3 parts of triethylamine was added, and the mixture was stirred at 28° to 33° C. for about 1 hour to finish the reaction. After the reaction, the reaction product was diluted with methylene chloride, washed with water, acidified with hydrochloric acid and then washed with water. When the electric conductivity of the aqueous phase was almost equivalent to that of ion-exchanged water, a methylene chloride phase was separated and dehydrated over dry anhydrous sodium sulfate. Then, 50.4 parts of benzoyl chloride was added, and 28.5 parts of pyridine was added. The mixture was stirred for about 1 hour to finish the reaction. After the reaction, the reaction mixture was filtered to remove hydrochloride of pyridine, acidified with hydrochloric acid and washed with water. When the electric conductivity of the aqueous phase was almost equivalent to that of ion-exchanged water, methylene chloride was evaporated to give 1,165.2 parts of a modified polycarbonate (yield 93%). In this polymer, almost no terminal hydroxyl group was detected by IR spectrum analysis. This polymer had a specific viscosity of 0.394, a glass transition temperature of 105° C., an MFR of 26 g/10 minutes, a total light transmittance of 89% and an impact strength of 45 kg.cm/cm.

EXAMPLE 13

The same reaction vessel as that used in Example 3 was charged with 4,206.2parts of ion-exchanged water and 295.2 parts of a 48% sodium hydroxide aqueous solution, and 811.7 parts of bisphenol A and 2.4 parts of hydrosulfite were dissolved in the charged mixture. Then, 2,589.4 parts of methylene chloride was added, and 387.5 parts of phosgene was blown into the mixture under the same conditions as those in Example 3. After the introduction of the phosgene was finished, a solution of 496.3 parts of the substituted phenol compound B, whose alcohol terminal group was acetylated, in 800 parts of methylene chloride was added, and 148.5 parts of a 48% sodium hydroxide aqueous solution and 79.2 parts of bisphenol A were added to emulsify the mixture. Thereafter, 3 parts of triethylamine was added, and the mixture was stirred at 28° to 33° C. for about 1 hour to finish the reaction. The reaction mixture was purified in the same manner as in Example 3 to give 1,315.2 parts of a modified polycarbonate (yield 94%). In this polymer, almost no terminal hydroxyl group was detected by IR absorption spectrum analysis, and this polymer had a specific viscosity of 0.360 and a glass transition temperature of 37° C. This polymer was dry-blended with 20% of glass fiber chopped strands (3 PE-455 FB, supplied by Nitto Boseki Co., Ltd.) and the blend was extruded in the form of pellets. The pellets were injection-molded to prepare a plate having a thickness of 3 mm. The plate showed a tracking resistance, at 200 V, of at least 100 drops.

EXAMPLE 14

100 Parts of a polycarbonate from bisphenol A, having a specific viscosity of 0.405 (Panlite L-1225W, supplied by Teijin Chemicals Limited), was mixed with 69.8 parts of the modified polycarbonate obtained in Example 12, and the mixture was extruded with an extruder at 250° C. to prepare pellets. These pellets had a substituted phenol compound A content, when analyzed by IR absorption spectrum, of 5%, an MFR of 15 g/10 minutes, a total light transmittance of 89% and an impact strength of 84 kg.cm/cm.

EXAMPLE 15

100 Parts of a polycarbonate from bisphenol A, having a specific viscosity of 0.405 (Panlite L-1225W, supplied by Teijin Chemicals Limited) was mixed with 17.2 parts of the modified polycarbonate obtained in Example 13, and the mixture was extruded with an extruder at 250° C. to prepare pellets. These pellets had a substituted phenol compound B content, when analyzed by IR absorption spectrum, of 5%, an MFR of 19 g/10 minutes, a total light transmittance of 89% and an Izod impact strength of 81 kg.cm/cm.

EXAMPLE 16

The same reaction vessel as that used in Example 3 was charged with 17,800 parts of ion-exchanged water and 3,732 parts of a 48.5% sodium hydroxide aqueous solution, and 3,131 parts of 1,1-bis(4-hydroxyphenyl)-3,3,5-trimethylcyclohexane was dissolved in the mixture. Then, 11,110 parts of methylene chloride was added, and while the mixture was stirred, 1,200 parts of phosgene was blown into the mixture at 20° C. over about 40 minutes. After the introduction of the phosgene was finished, the temperature inside the reaction vessel was increased up to 30° C., and 420.6 parts of the substituted phenol compound A was added to emulsify the reaction mixture. Then, 3.5 parts of triethylamine was added, and the mixture was stirred for about 1 hour and the reaction was finished. After the reaction, an organic phase was separated, diluted with methylene chloride, washed with water and then neutralized with hydrochloric acid. The resultant reaction product was repeatedly washed with water, and when the electric conductivity of the aqueous phase was almost equivalent to that of ion-exchanged water, an organic phase was separated and dehydrated with anhydrous sodium sulfate. Then, 123.3 parts of phenyl chloroformate was added, 62.5 parts of pyridine was further added, and the mixture was stirred for about 1 hour to finish the reaction. After the reaction, the reaction mixture was filtered to remove hydrochloride of pyridine, washed with water and acidified with hydrochloric acid. The reaction product was repeatedly washed with water, and when the electric conductivity of the aqueous phase was equivalent to that of ion-exchanged water, the reaction product was pulverized with evaporating methylene chloride to give 3,730.8 parts of a colorless modified polycarbonate (yield 96%). In this polymer, almost no terminal hydroxyl group was detected by IR absorption spectrum analysis. This polymer had a specific viscosity of 0.341, a glass transition temperature of 177° C. and an MFR of 3.0 g/10 minutes. Then, 0.03% of tris-(nonylphenyl)phosphite, 0.05% of Irganox 1076 and 0.2% of stearic acid monoglyceride were added to the above polymer, and the mixture was melt-extruded at 280° C. to prepare pellets. The pellets were injection-molded to prepare a test piece (disk plate) having a diameter of 40 mm and a thickness of 1 mm. This test piece had a total light transmittance of 89%.

EXAMPLE 17

1,091.5 Parts (yield 97%) of a modified polycarbonate was obtained in the same manner as in Example 3 except that 165.8 parts of the substituted phenol compound A was replaced with 60.4 parts of the substituted phenol compound B and 33.9 parts of p-tert-butylphenol. This polymer had a substituted phenol compound B content, when analyzed by IR absorption spectrum, of 5.2%, a specific viscosity of 0.316, a glass transition temperature of 115° C., an MFR of 38 g/10 minutes, a total light transmittance of 89% and an impact strength of 32 kg.cm/cm.

EXAMPLE 18

A reactor having a thermometer, a stirrer and a reflux condenser was charged with 4,954 parts of ion-exchanged water and 716.9 parts of a 48% sodium hydroxide aqueous solution, and 955.9 parts of bisphenol A and 0.95 parts of hydrosulfite were dissolved in the charged mixture. Then, 3,049.5 parts of methylene chloride was added, and while the mixture was stirred, 456.3 parts of phosgene was blown into the mixture at 15° to 20° C. over 60 minutes. After the introduction of the phosgene was finished, a solution of 165.8 parts of the substituted phenol compound A in 400 parts of methylene chloride was added, and 360.6 parts of a 48% sodium hydroxide aqueous solution and 93.3 parts of bisphenol A were add ed to emulsify the mixture. Thereafter, 3 parts of triethylamine was added, and the mixture was stirred at 28° to 33° C. for about 2 hours to finish the reaction. The reaction mixture was diluted with methylene chloride, washed with water and then acidified with hydrochloric acid. When the electric conductivity of the aqueous phase was almost equivalent to that of ion-exchanged water, methylene chloride was evaporated to give 1,130 parts of a colorless polymer (yield 92%). This polymer had a substituted phenol compound A content, when analyzed by IR absorption spectrum, of 12.3%, a specific viscosity of 0.390, an MFR of 38 g/10 minutes, a total light transmittance of 89%, a photoelasticity constant of $68 \times 10^{-13}$ cm$^2$/dyn and an Abbe's number of 33.

EXAMPLE 19

The same reactor as that used in Example 18 was charged with 4,206.2 parts of ion-exchanged water and 961.2 parts of a 48% sodium hydroxide aqueous solution, and 1,103.6 parts of 1,1-bis(4-hydroxyphenyl)-3,3,5-trimethylcyclohexane and 2.4 parts of hydrosulfite were dissolved in the charged mixture. Then, 2,589.4 parts of methylene chloride was added, and 422.9 parts of phosgene was blown into the mixture under the same conditions as those in Example 18. After the introduction of the phosgene was finished, a solution of 487.8 parts of the substituted phenol compound B in 800 parts of methylene chloride was added, and 306.2 parts of a 48% sodium hydroxide aqueous solution was added. Thereafter, the procedures in Example 18 were repeated to give 1,615 parts of a polymer (yield 96%). This polymer had a substituted phenol compound B content, when analyzed by absorption spectrum, of 24%, a specific viscosity of 0.340, a total light transmittance of 89%, photoelasticity constant of $22 \times 10^{-13}$ cm$^2$/dyn and an Abbe's number of 36.

EXAMPLE 20

The same reactor as that used in Example 18 was charged with 21,774 parts of ion-exchanged water, 1,428.2 parts of a 48% sodium hydroxide aqueous solution and 2.4 parts of hydrosulfite, and 606.8 parts of 9,9-bis(4-hydroxyphenyl)fluorene and 592.2 parts of bisphenol A were dissolved in the charged mixture. Then, 12,880 parts of methylene chloride was added, and 600 parts of phosgene was blown into the mixture at 20° to 26° C. over 60 minutes. After the introduction of the phosgene was finished, 178.5 parts of a 48% sodium hydroxide aqueous solution and a Solution of 468 parts of the substituted phenol compound B in 700 parts of methylene chloride were added to emulsify the mixture, and 2.5 parts of triethylamine was added. The mixture was stirred at 28° to 33° C. for 2 hours to finish the reaction. After the reaction, the procedures in Example 18 were repeated to give 1,689 parts of a polymer (yield 95%). This polymer had a substituted phenol compound B content, when analyzed by IR absorption spectrum of 25%, an MFL of 5 g/10 minutes, a specific viscosity of 0.316, a total light transmittance of 89%, a photoelasticity constant of $38 \times 10^{-13}$ cm$^2$/dyn and a refractive index of 1.610.

COMPARATIVE EXAMPLE 4

An aromatic polycarbonate resin which was produced from bisphenol A and phosgene by a conventional method and had a viscosity-average molecular weight of 22,500 (Panlite L-1225, supplied by Teijin Chemicals Limited) had a total light transmittance of 89%, a photoelasticity constant of $82 \times 10^{-13}$ cm$^2$/dyn, a refractive index of 1.589 and an Abbe's number of 30.

COMPARATIVE EXAMPLE 5

The same reactor as that used in Example 18 was charged with 221.3 parts of ion-exchanged water, 46.4 parts of a 48% sodium hydroxide aqueous solution and 0.04 part of hydrosulfite, and 38.9 parts of 1,1-bis(4-hydroxyphenyl)-3,3,5-trimethylcyclohexane was dissolved in the charged mixture. Then, 138 parts of methylene chloride was added, and 14.9 parts of phosgene was blown into the mixture at 15° to 20° C. over 45 minutes. After the introduction of the phosgene was finished, 0.57 part of p-tert-butylphenol was added to emulsify the mixture, and 0.04 part of triethylamine was added. Thereafter, the procedures in Example 19 were repeated to give 37.8 parts oil a polymer (yield 90%). This polymer had a specific viscosity of 0.336. This polymer showed poor melt fluidity, and when this polymer was forcibly molded into a disk having a diameter of 120 mm and a thickness of 1.2 mm, the disk was poor in hue, and had a total light transmittance of 87%. This polymer had a photoelasticity constant of $32 \times 10^{-13}$ cm$^2$/dyn, a refractive index of 1.553 and an Abbe's number of 33.

COMPARATIVE EXAMPLE 6

The same reactor as that used in Example 18 was charged with 27,180 parts of ion-exchanged water, 1,785.2 parts of a 48% sodium hydroxide aqueous solution and 3 parts of hydrosulfite, and 758.5 parts of 9,9-bis(4-hydroxyphenyl)fluorene and 740.3 parts of bisphenol A were dissolved in the charged mixture. Then, 16,100 parts of methylene chloride was added, and 750 parts of phosgene was blown into the mixture at 18° to 25° C. over 60 minutes. After the introduction of the phosgene was finished, 36.5 parts of p-tert-butylphenol and 223.1 parts of a 48% sodium hydroxide aqueous solution were added to emulsify the mixture, and 3 parts of triethylamine was added. The mixture was continuously stirred for 2 hours to finish the reaction. After the reaction, the procedures in Example 18 were repeated to give 1,556 parts of a polymer (yield 93%). This polymer had an MFR of 1 g/10 minutes, a specific viscosity of 0.309, a total light transmittance of 88%, a photoelasticity constant of $47 \times 10^{-13}$ cm$^2$/dyn and a refractive index of 1.616.

EXAMPLE 21

A reaction vessel having a phosgene-introducing tube and a reflux condenser was charged with 17,800 parts of ion-exchanged water and 3,732 parts of a 48.5% sodium hydroxide aqueous solution, and 3,131 parts of 1,1-bis(4-hydroxyphenyl)-3,3,5-trimethylcyclohexane was dissolved in the mixture. Then, 11,110 parts of methylene chloride was added, and while the mixture was vigorously stirred, 1,200 parts of phosgene was blown into the mixture at 20° C. over about 40 minutes to allow the mixture to react. After the introduction of the phosgene was finished, the temperature inside the reaction vessel was increased up to 30° C., and 420.6 parts of the substituted phenol compound A was added to emulsify the reaction mixture. Then, 3.5 parts of triethylamine was added, and the mixture was continuously stirred for about 2 hours and the reaction was finished. After the reaction, an organic phase was separated, diluted with methylene chloride, washed with water and then neutralized with hydrochloric acid. The resultant reaction product was repeatedly washed with water, and when the electric conductivity of the aqueous phase was almost equivalent to that of ion-exchanged water, an organic phase was separated and pulverized while methylene chloride was evaporated to give a powder (yield 99.5%). This powder had a specific viscosity of 0.339, a glass transition temperature of 175° C. and an MFR (280° C.) of 2.0 g/10 minutes. Then, 0.03% of tris-(nonylphenyl)phosphite, 0.05% of Irganox 1076 and 0.2% of stearic acid monoglyceride were added to the above powder, and the mixture was melt-extruded at 280° C. to prepare pellets. The pellets were injection-molded to prepare

25 a test piece (disk plate) having a diameter of 40 mm and a thickness of 1 mm. This test piece had a total light transmittance of 89%.

EXAMPLE 22

A powder was obtained in the same manner as in Example 21 except that the amount of the substituted phenol compound A was changed to 350.5 parts and that 15.2 parts of p-tert-butylphenol was further used (yield 99%). This powder had a specific viscosity of 0.293, a glass transition temperature of 176° C. and an MFR of 2.5 g/10 minutes. The same additives as those used in Example 21 were added to the powder, and the resultant composition was molded and evaluated in the same manner as in Example 21 to show a total light transmittance of 89%.

EXAMPLE 23

A powder was obtained in, the same manner as in Example 21 except that the amount of the substituted phenol compound A was changed to 350.5 parts and that 30.3 parts of p-tert-butylphenol was further used (yield 99%). This powder had a specific viscosity of 0.253, a glass transition temperature of 173° C. and an MFR of 4.0 g/10 minutes. The same additives as those used in Example 21 were added to the powder, and the resultant composition was molded and evaluated in the same manner as in Example 21 to show a total light transmittance of 90%.

EXAMPLE 24

A powder was obtained in the same manner as in Example 21 except that the amount of the substituted phenol compound A was changed to 210.3 parts and that 45.5 parts of p-tert-butylphenol was further used (yield 98.5%). This powder had a specific viscosity of 0.290, a glass transition temperature of 180° C. and an MFR of 2.0 g/10 minutes. The same additives as those used in Example 21 were added to the polymer, and the resultant composition was molded and evaluated in the same manner as in Example 21 to show a total light transmittance of 90%.

COMPARATIVE EXAMPLE 7

A polycarbonate resin obtained from bisphenol A having a specific viscosity of 0.451 was evaluated in the same manner as in Example 21. This polycarbonate resin had a glass transition temperature of 150° C., an MFR of 8.0 g/10 minutes and a total light transmittance of 89%.

COMPARATIVE EXAMPLE 8

A powder was obtained in, the same manner as in Example 21 except that the substituted phenol compound A was replaced with 90.9 parts of p-tert-butylphenol (yield 99.6%). This powder had a specific viscosity of 0.248, a glass transition temperature of 227° C. and an MFR of 0.3 g, and it was poor in melt fluidity. A test piece was prepared from the above powder in the same manner as in Example 21 to show that the test piece had a burn mark and that the total light transmittance decreased to 83%.

EXAMPLE 25

A reactor having a thermometer, a stirrer and a reflux condenser was charged with 17,800 parts of ion-exchanged water and 3,732 parts of a 48% sodium hydroxide aqueous solution, and 3,131.3 parts of 1,1-bis(4-hydroxyphenyl)-3, 3,5-trimethylcyclohexane and 3.1 parts of hydrosulfite were dissolved in the mixture. Then, 11,110 parts of methylene chloride was added, and while the mixture was stirred, 1,200 parts of phosgene was blown into the mixture at 15° to 20° C. over 40 minutes. After the introduction of the phosgene was finished, a solution of 1,318.7 parts of the substituted phenol compound C in 4,500 parts of methylene chloride was added to emulsify the reaction mixture. Then, 3.5 parts of triethylamine was added, and the mixture was stirred at 28° to 33° C. for about 2 hours and the reaction was finished. After the reaction, the reaction product was diluted with methylene chloride, washed with water and then acidified with hydrochloric acid. The resultant reaction product was washed with water, and when the electric conductivity of the aqueous phase was almost equivalent to that of ion-exchange d water, methylene chloride was evaporated to give a colorless polymer (yield 96.5%). This polymer had a specific viscosity, $\eta_{sp}$, of 0.289, a Tg of 128° C., an MFR of 55 g/10 minutes and a lactone monomer unit content of 51.9 mol %. This polymer was injection-molded with a DISK 5 MILL supplied by Sumitomo Heavy Industries, Ltd. to prepare a disk having a diameter of 80 mm and a thickness of 1.2 mm. The so-obtained disk had a total light transmittance of 89%, a photoelasticity constant of $24 \times 10^{-13}$ cm$^2$/dyn and an oblique incidence birefringence phase difference of 20 nm.

EXAMPLE 26

A reactor having a thermometer, a stirrer and a reflux condenser was charged with 17,800 parts of ion-exchanged water and 3,732 parts of a 48% sodium hydroxide aqueous solution, and 3,131.3 parts of 1,1-bis(4-hydroxyphenyl)-3, 3,5-trimethylcyclohexane and 3.1 parts of hydrosulfite were dissolved in the mixture. Then, 11,110 parts of methylene chloride was added, and while the mixture was stirred, 1,200 parts of phosgene was blown into the mixture at 15° to 20° C. over 40 minutes. After the introduction of the phosgene was finished, a solution of 879.1 parts of the substituted phenol compound C and 30.3 parts of p-tert-butylphenol in 4,000 parts of methylene chloride was added. Thereafter, the procedures in Example 25 were repeated to give a colorless polymer (yield 96%). This polymer had a specific viscosity, $\eta_{sp}$, of 0.273, a Tg of 143° C., an MFR of 50 g/10 minutes and a lactone monomer unit content of 42.0 mol %. This polymer was injection-molded in the same manner as in Example 25, and the resultant disk was evaluated in the same manner as in Example 25 to show that it had a total light transmittance of 89%, a photoelasticity constant of $26 \times 10^{-13}$ cm$^2$/dyn and an oblique incidence birefringence phase difference of 25 nm.

EXAMPLE 27

A reactor having a thermometer, a stirrer and a reflux condenser was charged with 17,800 parts of ion-exchanged water and 3,732 parts of a 48% sodium hydroxide aqueous solution, and 2,191.7 parts of 1,1-bis(4-hydroxyphenyl)-3, 3,5-trimethylcyclohexane, 690.8 parts of bisphenol A and 3.1 parts of hydrosulfite were dissolved in the mixture. Then, 11,110 parts of methylene chloride was added, and while the mixture was stirred, 1,200 parts of phosgene was blown into the mixture at 15° to 20° C. over 40 minutes. After the introduction of the phosgene was finished, a solution of 926.2 parts of the substituted phenol compound D in 4,200 parts of methylene chloride was added. Thereafter, the procedures in Example 25 were repeated to give a colorless polymer (yield 95%). This polymer had a specific viscosity, $\eta_{sp}$, of 0.320, a Tg of 135° C., an MFR of 45 g/10 minutes and a lactone monomer unit content of 43 mol %. This polymer was injection-molded in the same manner as in Example 25, and the resultant disk was evaluated in the same manner as in Example 25 to show that it had a total light transmittance of 89%, a photoelasticity constant of $38 \times 10^{-13}$ cm$^2$/dyn and an oblique incidence birefringence phase difference of 28 nm.

EXAMPLE 28

A reactor having a thermometer, a stirrer and a reflux condenser was charged with 17,800 parts of ion-exchanged water and 3,732 parts of a 48% sodium hydroxide aqueous solution, and 1,565.5 parts of 1,1-bis(4-hydroxyphenyl)-3,3,5-trimethylcyclohexane, 1,151.4 parts of 1,1-bis(4-hydroxyphenyl)-1-phenylethane and 3.1 parts of hydrosulfite were dissolved in the mixture. Thereafter, the procedures in Example 25 were repeated to give a colorless polymer (yield 96.8%). This polymer had a specific viscosity, $\eta_{sp}$, of 0.270, a Tg of 138° C., an MFR of 60 g/10 minutes and a lactone monomer unit content of 51.9 mol %. This polymer was injection-molded in the same manner as in Example 25, and the resultant disk was evaluated in the same manner as in Example 25 to show that it had a total light transmittance of 89%, a photoelasticity constant of $33 \times 10^{-13}$ cm$^2$/dyn and an oblique incidence birefringence phase difference of 25 nm.

COMPARATIVE EXAMPLE 9

A polycarbonate resin having a specific viscosity, $\eta_{sp}$, of 0.284 and produced from bisphenol A and phosgene by a conventional method (Panlite AD-5503, supplied by Teijin Chemicals Limited) was molded in the same manner as in Example 25, and the resultant disk was evaluated in the same manner as in Example 25 to show that it had a total light transmittance of 89%, a photoelasticity constant of $82 \times 10^{-13}$ cm$^2$/dyn and an oblique incidence birefringence phase difference of 68 nm.

COMPARATIVE EXAMPLE 10

A polymer was obtained in the same manner as in Example 25 except that the substituted phenol compound C was replaced with 90.9 parts of p-tert-butylphenol (yield 95%). This polymer had a specific viscosity, $\eta_{sp}$, of 0.248 and an MFR of 0.3. This polymer had too poor melt fluidity to be molded into a disk.

EXAMPLE 29

A reactor having a thermometer, a stirrer and a reflux condenser was charged with 4,206.2 parts of ion-exchanged water and 295.2 parts of a 48% sodium hydroxide aqueous solution, and 811.7 parts of bisphenol A and 0.95 part of hydrosulfite were dissolved in the mixture. Then, 2,589.4 parts of methylene chloride was added, and while the mixture was stirred, 387.5 parts of phosgene was blown into the mixture at 15° to 20° C. over 60 minutes. After the introduction of the phosgene was finished, a solution of 487.8 parts of the substituted phenol compound B in 800 parts of methylene chloride was added, and further, 148.5 parts of a 48% sodium hydroxide aqueous solution and 79.2 parts of bisphenol A were added to emulsify the reaction mixture. Then, 2.5 parts of triethylamine was added, the mixture was stirred at 28° to 33° C. for about 2 hours, and the reaction was finished. After the reaction, the reaction product was diluted with methylene chloride, washed with water and then acidified with hydrochloric acid. The resultant reaction product was washed with water, and when the electric conductivity of the aqueous phase was almost equivalent to that of ion-exchanged water, methylene chloride was evaporated to give 1,321.4 parts of a colorless polymer (yield 95%). This polymer had a polycaprolactone portion content, analyzed by IR absorption spectrum, of 34.3% by weight, a specific viscosity of 0.355 and a refractive index of 1.580.

EXAMPLE 30

The same reactor as that used in Example 29 was charged with 17,800 parts of ion-exchanged water and 3,732 parts of a 48% sodium hydroxide aqueous solution, and 3,131 parts of 1,1-bis(4-hydroxyphenyl)- 3,3,5-trimethylcyclohexane was dissolved in the mixture. Then, 11,110 parts of methylene chloride was added, and while the mixture was vigorously stirred, 1,200 parts of phosgene was blown into the mixture at 20° C. over about 40 minutes. After the introduction of the phosgene was finished, the temperature inside the reactor was increased to 30° C., and 420.6 parts of the substituted phenol compound A was added to emulsify the reaction mixture. Then, 3.5 parts of triethylamine was added, and the mixture was continuously stirred for about 2 hours and the reaction was finished. After the reaction, the procedures in Example 29 were repeated to give a polymer (yield 99.5%). This polymer had a polycaprolactone portion content, analyzed by IR absorption spectrum, of 9.7% by weight, a specific viscosity of 0.339 and a refractive index of 1.553.

COMPARATIVE EXAMPLE 11

The same reactor as that used in Example 29 was charged with 4,206.2 parts of ion-exchanged water and 295.2 parts of a 48% sodium hydroxide aqueous solution, and 811.7 parts of bisphenol A was dissolved in the mixture. Then, 2,589.4 parts of methylene chloride was added, and while the mixture was vigorously stirred, 387.5 parts of phosgene was blown into the mixture at 20° C. over about 40 minutes. Then, the temperature inside the reactor was increased to 30° C., and 30.4 parts of p-tert-butylphenol was added to emulsify the reaction mixture. Then, 2.5 parts of triethylamine was added, and the mixture was continuously stirred for about 2 hours and the reaction was finished. After the reaction, the procedures in Example 29 were repeated to give a polymer (yield 99%). This polymer had a specific viscosity of 0.293 and a refractive index of 1.585.

COMPARATIVE EXAMPLE 12

A polymer was obtained in the same manner as in Example 30 except that the substituted phenol compound A was replaced with 90.9 parts of p-tert-butylphenol (yield 99%). This polymer had a specific viscosity of 0.248 and a refractive index of 1.556.

EXAMPLE 31

80.0 Parts of the polymer obtained in Example 29 was mixed with 20.0 parts of a glass fiber having a refractive index of 1.579 (average fiber diameter 24 μm, an average fiber length 6 mm), and the mixture was extruded with an extruder (VSK-30, supplied by Nakatani K.K.) at a cylinder temperature of 260° C. to prepare pellets. The pellets were injection-molded with an injection molding machine (Nestar.Cycap, 480/150, supplied by Sumitomo Heavy Industries, Ltd.) at a cylinder temperature of 290° C. at a mold temperature of 90° C. to prepare a test piece having a size of 50 mm×50 mm×2 mm, and the test piece was measured for a fog value to show 17%.

EXAMPLE 32

80.0 Parts of the polymer obtained in Example 30 was mixed with 20.0 parts of a glass fiber having a refractive index of 1.545 (average fiber diameter 13 μm, an average fiber length 3 mm), and a test piece was prepared from the mixture in the same manner as in Example 29 and measured for a fog value to show 19%.

COMPARATIVE EXAMPLE 13

80.0 Parts of the polymer obtained in Comparative Example 11 was mixed with 20.0 parts of the same glass fiber having a refractive index of 1.579 as that used in Example 31, and a test piece was prepared from the mixture in the same manner as in Example 31 and measured for a fog value to show 41%.

COMPARATIVE EXAMPLE 14

80.0 Parts of the polymer obtained in Comparative Example 12 was mixed with 20.0 parts of the same glass fiber having a refractive index of 1.545 as that used in Example 32, and a test piece was prepared from the mixture in the same manner as in Example 31 and measured for a fog value to show 54%.

EXAMPLES 33–35

A reactor having a thermometer, a stirrer and a reflux condenser was charged with 4,206.2 parts of ion-exchanged water and 961.2 parts of a 48% sodium hydroxide aqueous solution, and 1103.6 parts of 1,1-bis(4-hydroxyphenyl)-3,3,5-trimethylcyclohexane and 2.4 parts of hydrosulfite were dissolved in the mixture. Then, 2,589.4 parts of methylene chloride was added, and while the mixture was stirred, 422.9 parts of phosgene was blown into the mixture at 15° to 20° C. over 60 minutes. After the introduction of the phosgene was finished, a solution of 487.8 parts of the substituted phenol compound B in 800 parts of methylene chloride was added, and further, 306.2 parts of a 48% sodium hydroxide aqueous solution was added to emulsify the reaction mixture. Then, 3 parts of triethylamine was added, the mixture was stirred at 28° to 33° C. for about 2 hours, and the reaction was finished. After the reaction, the reaction product was diluted with methylene chloride, washed with water and then acidified with hydrochloric acid. The resultant reaction product was washed with water, and when the electric conductivity of the aqueous phase was almost equivalent to that of ion-exchanged water, methylene chloride was evaporated to give 1,615 parts of a colorless polymer (yield 96%). This polymer had a specific viscosity of 0.340 and a polycaprolactone portion content, analyzed by IR absorption spectrum, of 24% by weight. This polymer was extrusion-molded to prepare a sheet having a width of 100 cm, a length of 70 cm and a thickness of 0.2 mm (Example 33), 0.4 mm (Example 34) or 1.2 mm (Example 35), and these sheets were measured for warpages and retardations. Table 1 shows the results.

EXAMPLES 36–38

The same reactor as that used in Example 33 was charged with 21,774 parts of ion-exchanged water, 1,428.2 parts of a 48% sodium hydroxide aqueous solution and 2.4 parts of hydrosulfite, and 606.8 parts of 9,9-bis(4-hydroxyphenyl)fluorene and 592.2 parts of bisphenol A were dissolved in the mixture. Then, 12,880 parts of methylene chloride was added, and 600 parts of phosgene was blown into the mixture at 20° to 26° C. over 60 minutes. After the introduction of the phosgene was finished, 178.5 parts of a 48% sodium hydroxide aqueous solution and a solution of 468 parts of the substituted phenol compound B in 700 parts of methylene chloride were added to emulsify the mixture. Then, 2.5 parts of triethylamine was added, the mixture was stirred at 28° to 33° C. for about 2 hours, and the reaction was finished. After the reaction, the reaction product was treated in the same manner as in Example 33 to give 1,689 parts of a polymer (yield 95%). This polymer had a specific viscosity of 0.316 and a polycaprolactone portion content, analyzed by IR absorption spectrum, of 25% by weight. This polymer was extrusion-molded to prepare sheets similar to those obtained in Examples 33 to 35, and these sheets were measured for warpages and retardations. Table 1 shows the results.

COMPARATIVE EXAMPLES 15–17

A polycarbonate from bisphenol A, having a specific viscosity of 0.451 (Panlite L-1250, supplied by Teijin Chemicals Limited), was extrusion-molded to prepare sheets similar to those obtained in Examples 33 to 35, and these sheets were measured for warpages and retardations. Table 1 shows the results.

TABLE 1

| | Thickness of sheet (mm) | Retardation in width direction (nm) Distance (cm) from end portion | | | | | | | | | Percentage of warpage of sheet (%) |
|---|---|---|---|---|---|---|---|---|---|---|---|
| | | 10 | 20 | 30 | 40 | 50 | 60 | 70 | 80 | 90 | |
| Ex. 33 | 0.2 | 3 | 2 | 2 | 2 | 2 | 2 | 3 | 3 | 3 | 0.3 |
| Ex. 34 | 0.4 | 4 | 3 | 2 | 2 | 2 | 2 | 3 | 3 | 4 | 0.3 |
| Ex. 35 | 1.2 | 5 | 4 | 3 | 3 | 3 | 3 | 3 | 4 | 4 | 0.4 |
| Ex. 36 | 0.2 | 3 | 3 | 2 | 2 | 2 | 2 | 2 | 3 | 3 | 0.2 |
| Ex. 37 | 0.4 | 4 | 3 | 3 | 2 | 2 | 2 | 3 | 3 | 3 | 0.3 |
| Ex. 38 | 1.2 | 5 | 4 | 4 | 3 | 3 | 3 | 4 | 4 | 5 | 0.3 |
| CEx. 15 | 0.2 | 85 | 60 | 55 | 43 | 43 | 52 | 57 | 65 | 83 | 0.2 |
| CEx. 16 | 0.4 | 97 | 74 | 56 | 50 | 51 | 57 | 66 | 87 | 102 | 0.2 |
| CEx. 17 | 1.2 | 125 | 102 | 98 | 83 | 82 | 84 | 96 | 107 | 128 | 0.3 |

EXAMPLE 39

A reactor having a thermometer, a stirrer and a reflux condenser was charged with 383.5 parts of ion-exchanged water and 80.4 parts of a 48% sodium hydroxide aqueous solution, and 67.5 parts of 1,1-bis(4-hydroxyphenyl)-3,3,5-trimethylcyclohexane and 0.07 part of hydrosulfite were dissolved in the mixture. Then, 289 parts of methylene chloride was added, and while the mixture was stirred, 28 parts of phosgene was blown into the mixture at 15° to 20°

C. over 60 minutes. After the introduction of the phosgene was finished, a solution of 15.8 parts of the substituted phenol compound E and 1.0 part of p-tert-butylphenol in 50 parts of methylene chloride was added to emulsify the mixture. Then, 0.05 part of triethylamine was added, the mixture was stirred at 28° to 33° C. for about 1 hour, and the reaction was finished. After the reaction, the reaction product was diluted with methylene chloride, washed with water and then acidified with hydrochloric acid. The resultant reaction product was washed with water, and when the electric conductivity of the aqueous phase was almost equivalent to that of ion-exchanged water, methylene chloride was evaporated to give 1,615 parts of a colorless polymer (yield 93%).

This polymer had a specific viscosity, measured in a concentration of 0.7 g/100 ml using methylene chloride as a solvent, of 0.296 and a glass transition temperature of 118° C. It had a polycaprolactone portion content, analyzed by IR absorption spectrum, of 17.7% by weight. It has an MFR of 50 g/10 minutes, a total light transmittance of 89% and a photoelasticity constant of $28 \times 10^{-13}$ cm$^2$/dyn.

EXAMPLE 40

A reactor having a thermometer, a stirrer and a reflux condenser was charged with 3,006 parts of ion-exchanged water and 198 parts of a 48% sodium hydroxide aqueous solution, and 228 parts of bisphenol A was dissolved in the mixture. Then, a solution of 16 parts of the substituted-phenol compound A in 2,465 parts of methylene chloride was added, and while the mixture was stirred, 83.4 parts of phosgene was blown into the mixture at 15° to 18° C. over 25 minutes. As soon as the introduction of the phosgene was started, a solution of 67.6 parts of terephthalic acid and 1.8 parts of p-tert-butylphenol in 1,000 parts of methylene chloride was added dropwise over about 15 minutes. After the introduction of the phosgene was finished, 41.2 parts of a 48% sodium hydroxide aqueous solution was added to emulsify the reaction mixture. Then, 0.6 part of triethylamine was added, the mixture was stirred at 28° to 33° C. for about 1 hour, and the reaction was finished. After the reaction, the reaction product was diluted with methylene chloride, washed with water and then acidified with hydrochloric acid. The resultant reaction product was washed with water, and when the electric conductivity of the aqueous phase was almost equivalent to that of ion-exchanged water, methylene chloride was evaporated to give 361.3 parts of a colorless polymer (yield 92%). This polymer had a specific viscosity of 0.393, a glass transition temperature of 135° C., an MFR of 23 g/10 minutes and a total light transmittance of 89%.

For comparison, 316.6 parts (yield 96%) of a polymer was obtained in the same manner as above except that 16 parts of the substituted phenol compound A was replaced with 6 parts of p-tert-butylphenol. This polymer had a specific viscosity of 0.425, a glass transition temperature of 165° C., an MFR of 2.5 g/10 minutes and a total light transmittance of 89%.

EXAMPLE 41

The same reactor as that used in Example 40 was charged with 507 parts of ion-exchanged water and 33.3 parts of a 48% sodium hydroxide aqueous solution, and 20.7 parts of bisphenol A, 3.5 parts of 9,9-bis(4-hydroxyphenyl)fluorene and 2.4 parts of hydrosulfite were dissolved in the mixture. Then, a solution of 2.8 parts of the substituted phenol compound A in 301 parts of methylene chloride was added, and 8 parts of phosgene was blown into the mixture under the same conditions as those in Example 40. As soon as the introduction of the phosgene was started, a solution of 8.8 parts of terephthalic acid dichloride in 100 parts of methylene chloride was added dropwise in the same manner as in Example 40. After the introduction of the phosgene was finished, 0.06 part of triethylamine was added, and thereafter, the procedures in Example 40 were repeated to give 32 parts of a polymer (yield 94%). This polymer had a specific viscosity of 0.400, a glass transition temperature of 142° C. and an MFR of 20 g/10 minutes.

For comparison, 27.9 parts (yield 89%) of a polymer was obtained in the same manner as above except that 2.8 parts of the substituted phenol compound A was replaced with 0.6 part of p-tert-butylphenol. This polymer had a specific viscosity of 0.435, a glass transition temperature of 188° C., an MFR of 4.3 g/10 minutes and a total light transmittance of 88%.

EXAMPLE 42

The same reactor as that used in Example 40 was charged with 491.3 parts of ion-exchanged water and 32.5 parts of a 48% sodium hydroxide aqueous solution, and 57 parts of 1,3-bis(4-hydroxyphenyl)-5,7-dimethyladamantane and 0.08 part of hydrosulfite were dissolved in the mixture. Then, a solution of 7.9 parts of the substituted phenol compound B in 398 parts of methylene chloride was added, and while the mixture was stirred, 8.1 parts of phosgene was blown into the mixture at 15° to 25° C. over 30 minutes. As soon as the introduction of the phosgene was started, a solution of 16.6 parts of terephthalic acid dichloride and 5.5 parts of isophthalic acid dichloride in 100 parts of methylene chloride was added over about 15 minutes. After the introduction of the phosgene was finished, 6.8 parts of a 48% sodium hydroxide aqueous solution and 0.14 part of triethylamine were added, and thereafter, the procedures in Example 40 were repeated and the reaction was finished. After the reaction, the reaction mixture was purified in the same manner as in Example 40 to give 73.2 parts of a polymer (yield 91%). This polymer had a specific viscosity of 0.333, a glass transition temperature of 154° C., an MFR of 2.5 g/10 minutes and a total light transmittance of 89%.

For comparison, 66 parts (yield 91%) of a polymer was obtained in the same manner as above except that 7.9 parts of the substituted phenol compound B was replaced with 0.5 part of p-tert-butylphenol. This polymer had a specific viscosity of 0.330 and a glass transition temperature of 274° C., and its fluidity was too poor to measure an MFR.

EXAMPLE 43

358.3 Parts (yield 91%) of a polymer was obtained in the same manner as in Example 40 except that 16 parts of the substituted phenol compound A was replaced with 17 parts of the substituted phenol compound A of which the alcohol terminal was acetylated. This polymer had a specific viscosity of 0.395, a glass transition temperature of 133° C., an MFR of 25 g/10 minutes and a total light transmittance of 90%.

EXAMPLE 44

A reactor having a thermometer, a stirrer and a reflux condenser was charged with a solution of 6.9 parts of isophthalic acid chloride, 3.3 parts of terephthalic acid chloride and 0.09 parts of tributylbenzylammonium chloride in 240 parts of methylene chloride, and while the mixture was stirred, 142.6 parts of ion-exchanged water, 8.6 parts of a 48% sodium hydroxide aqueous solution, a solution of 11.4 parts of bisphenol A in water and a solution of 1.9 parts of the substituted phenol compound A in 10 parts of methylene chloride were simultaneously added over about 30 seconds. The mixture was stirred for about 30 minutes and the reaction was finished. After the reaction, the product was diluted with methylene chloride, washed with water and acidified with hydrochloric acid. The resultant product was washed with water, and when the electric conductivity of the aqueous phase was almost equivalent to that of ion-exchanged water, methylene chloride was evaporated to give 16.6 parts of a colorless polymer (yield 92%). This polymer had a specific viscosity of 0.349, a glass transition temperature of 135° C., an MFR of 11 g/10 minutes, a total light transmittance of 87% and a notched Izod impact strength of 17 kg.cm/cm.

For comparison, 17.2 parts (yield 96%) of a polymer was obtained in the same manner as above except that 1.9 parts of the substituted phenol compound A was replaced with 0.41 part of p-tert-butylphenol. This polymer had a specific viscosity of 0.346, a glass transition temperature of 185° C., an MFR of 2.2 g/10 minutes, a total light transmittance of 87% and a notched Izod impact strength of 16 kg.cm/cm.

EXAMPLE 45

The same reactor as that used in Example 44 was charged with a solution of 4.55 parts of isophthalic acid chloride, 5.6 parts of terephthalic acid chloride and 0.09 parts of tributylbenzylammonium chloride in 240 parts of methylene chloride, and while the mixture was stirred, 142.6 parts of ion-exchanged water, 8.6 parts of a 48% sodium hydroxide aqueous solution, a solution of 11.4 parts of bisphenol A in water, 0.075 part of p-tert-butylphenol and a solution of 1.56 parts of the substituted phenol compound A in 10 parts of methylene chloride were simultaneously added over about 30 seconds. The mixture was stirred for about 30 minutes and the reaction was finished. After the reaction, the product was treated in the same manner as in Example 44 to give 17.2 parts of a polymer (yield 94%). This polymer had a specific viscosity of 0.354, a glass transition temperature of 138° C., an MFR of 10 g/10 minutes, a total-light transmittance of 88% and a notched Izod impact strength of 14 kg.cm/cm.

For comparison, 15.9 parts (yield 89%) of a polymer was obtained in the same manner as above except that 1.56 parts of the substituted phenol compound A was replaced with 0.335 part of p-tert-butylphenol. This polymer had a specific viscosity of 0.344, a glass transition temperature of 189° C., an MFR of 1.4 g/10 minutes, a total light transmittance of 88% and a notched Izod impact strength of 11 kg.cm/cm.

What is claimed is:

1. A modified aromatic polycarbonate resin comprising an aromatic polycarbonate resin having at least one substituted phenyloxy group of the following formula (I) in an amount of at least 5 mol % of the total amount of terminal groups of said polycarbonate resin,

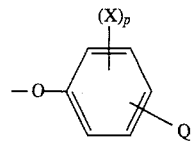

wherein:
X is a halogen atom or a monovalent aliphatic hydrocarbon group having 1 to 10 carbon atoms,
p is an integer of 0 to 4, and

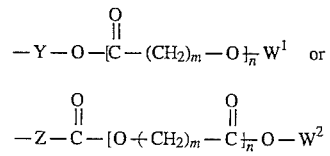

in which:
Y is a divalent aliphatic hydrocarbon group having 1 to 10 carbon atoms,
$W^1$ is a hydrogen atom,

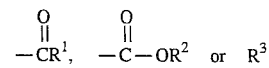

in which each of $R^1$, $R^2$ and $R^3$ is a monovalent aliphatic hydrocarbon group having 1 to 10 carbon atoms, a monovalent alicyclic hydrocarbon group having 4 to 8 carbon atoms or a monovalent aromatic hydrocarbon group having 6 to 15 carbon atoms,
m is an integer of 4 to 20,
n is an integer of 1 to 100,
Z is a single bond or a divalent aliphatic hydrocarbon group having 1 to 10 carbon atoms, and
$W^2$ is a hydrocarbon atom, a monovalent aliphatic hydrocarbon group having 1 to 10 carbon atoms, an alicyclic hydrocarbon group having 4 to 8 carbon atoms or a monovalent aromatic hydrocarbon group having 6 to 15 carbon atoms.

2. The resin of claim 1, wherein the modified aromatic polycarbonate resin is melt-moldable.

3. The resin of claim 1, wherein the modified aromatic polycarbonate resin has a specific viscosity of at least 0.165.

4. The resin of claim 1, wherein said aromatic polycarbonate resin is formed from at least one dihydric phenol compound which is at least one member selected from the group consisting of 2,2-bis(4-hydroxyphenyl)-propane, 2,2-bis(3-methyl-4-hydroxyphenyl)propane, 1,1-bis(4-hydroxyphenyl)cyclohexane, 2,2-bis(3-phenyl-4-hydroxyphenyl)propane, 2,2-bis(3-isopropyl-4-hydroxyphenyl)propane, 2,2-bis(4-hydroxyphenyl)butane, 9,9-bis(4-hydroxyphenyl)fluorene, 1,1-bis (4-hydroxyphenyl)-3,3,5-trimethylcyclohexane and 1,3-bis(4-hydroxyphenyl)-5,7-dimethyladamantane.

5. The resin of claim 1, wherein said aromatic polycarbonate resin is formed from at least one dihydric phenol compound which is at least one member selected from the group consisting of 2,2-bis(4-hydroxyphenyl)-propane, 1,1-bis(4-hydroxyphenyl)cyclohexane, 9,9-bis(4-hydroxyphenyl)fluorene, 1,1-bis(4-hydroxyphenyl)-3,3,5-trimethylcyclohexane and 1,3-bis(4-hydroxyphenyl)-5,7-dimethyladamantane.

6. The resin of claim 1, wherein in the formula (I) m is an integer of 4 to 10 and n is an integer of 3 to 50.

7. The resin of claim 1, wherein in the formula (I) the product of m times n is in the range of from 10 to 200.

8. The resin of claim 1, wherein the modified aromatic polycarbonate resin comprises at least one substituted phenyloxy group of the formula (I) in an amount of from 7 to 90 mol % of the total amount of terminal groups of said polycarbonate resin.

9. A molded article formed from the resin as recited in claim 1.

10. An optical information recording medium having a substrate formed from the resin as recited in claim 1.

11. A resin composition consisting essentially of
   (A) 40 to 95% by weight of the resin of claim 1, and
   (B) 60 to 5% by weight of a glass filler wherein the refractive index of the glass filler differs from the refractive index of (A) by 0.01 or less.

12. A modified aromatic polyester carbonate resin comprising an aromatic polyester carbonate resin having at least one substituted phenyloxy group of the following formula (I) in an amount of at least 5 mol % of the total amount of terminal groups of said polyester carbonate resin,

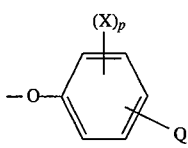

wherein:
   X is a halogen atom or a monovalent aliphatic hydrocarbon group having 1 to 10 carbon atoms,
   p is an integer of 0 to 4, and

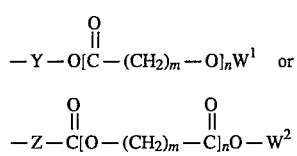

in which:
   Y is a divalent aliphatic hydrocarbon group having 1 to 10 carbon atoms,
   $W^1$ is a hydrogen atom,

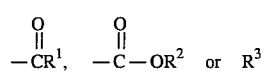

in which each of $R^1$, $R^2$, and $R^3$ is a monovalent aliphatic hydrocarbon group having 1 to 10 carbon atoms, a monovalent alicyclic hydrocarbon group having 4 to 8 carbon atoms or a monovalent aromatic hydrocarbon group having 6 to 15 carbon atoms,
   m is an integer of 4 to 20,
   n is an integer of 1 to 100,
   Z is a single bond or a divalent aliphatic hydrocarbon group having 1 to 10 carbon atoms, and
   $W^2$ is a hydrogen atom, a monovalent aliphatic hydrocarbon group having 1 to 10 carbon atoms, an alicyclic hydrocarbon group having 4 to 8 carbon atoms or a monovalent aromatic hydrocarbon group having 6 to 15 carbon atoms.

13. The resin of claim 12, wherein the modified aromatic polyester carbonate resin is melt-moldable.

14. The resin of claim 12, wherein said resin has an ester bond to carbonate bond molar ratio of from 5:95 to 75:25.

15. A molded article formed from the modified aromatic polyester carbonate resin as recited in claim 12.

16. A modified polyarylate resin comprising a polyarylate resin having at least one substituted phenyloxy group of the following formula (I) in an amount of at least 5 mol % of the total amount of terminal groups of said polyarylate resin,

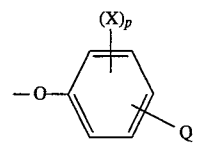

wherein:
   X is a halogen atom or a monovalent aliphatic hydrocarbon group having 1 to 10 carbon atoms,
   p is an integer of 0 to 4, and

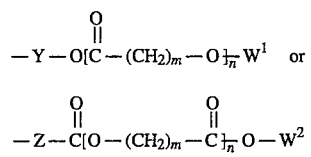

in which:
   Y is a divalent aliphatic hydrocarbon group having 1 to 10 carbon atoms,
   $W^1$ is a hydrogen atom,

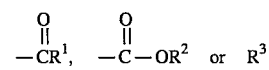

in which each of $R^1$, $R^2$, and $R^3$ is a monovalent aliphatic hydrocarbon group having 1 to 10 carbon atoms, a monovalent alicyclic hydrocarbon group having 4 to 8 carbon atoms or a monovalent aromatic hydrocarbon group having 6 to 15 carbon atoms,
   m is an integer of 4 to 20,
   n is an integer of 1 to 100,
   Z is a single bond or a divalent aliphatic hydrocarbon group having 1 to 10 carbon atoms, and
   $W^2$ is a hydrogen atom, a monovalent aliphatic hydrocarbon group having 1 to 10 carbon atoms, an alicyclic hydrocarbon group having 4 to 8 carbon atoms or a monovalent aromatic hydrocarbon group having 6 to 15 carbon atoms.

17. The resin of claim 16, wherein the modified polyarylate resin is melt-moldable, 18. A molded article formed from the modified polyarylate resin as recited in claim 16.

19. A substituted phenol compound of the formula (II),

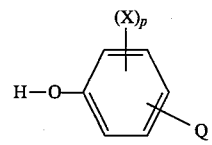

wherein:
   X is a halogen atom or a monovalent aliphatic hydrocarbon group having 1 to 10 carbon atoms,
   p is an integer of 0 to 4, and Q is 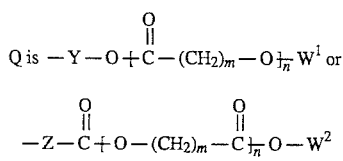 or

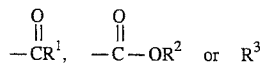

in which:

Y is a divalent aliphatic hydrocarbon group having 1 to 10 carbon atoms, $W^1$ is a hydrogen atom, $$-CR^1, \quad -C-OR^2 \quad or \quad R^3$$

in which each of $R^1$, $R^2$ and $R^3$ is a monovalent aliphatic hydrocarbon group having 1 to 10 carbon atoms, a monovalent alicyclic hydrocarbon group having 4 to 8 carbon atoms or a monovalent aromatic hydrocarbon group having 6 to 15 carbon atoms, m is an integer of 4 to 20, n is an integer of 1 to 100, z is a single bond or a divalent aliphatic hydrocarbon group having 1 to 10 carbon atoms, and $W^2$ is a hydrogen atom, a monovalent aliphatic hydrocarbon group having 1 to 10 carbon atoms, an alicyclic hydrocarbon group having 4 to 8 carbon atoms or a monovalent aromatic hydrocarbon group having 6 to 15 carbon atoms.

20. The molded article of claim 9 wherein said article is a lens.

21. The substituted phenol compound of claim 19 wherein Q is the group

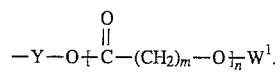

22. The substituted phenol compound of claim 19 wherein Q is the group

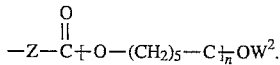

23. The substituted phenol compound of claim 21 having the formula

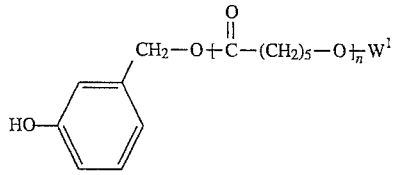

wherein $W^1$ represents a hydrogen atom or —$OCH_3$.

24. The modified aromatic polycarbonate resin of claim 1 wherein said polycarbonate resin has an intrinsic viscosity within the range of from 0.229 to 0.539.

25. The modified aromatic polycarbonate resin of claim 1 wherein said polycarbonate resin has an intrinsic viscosity of less than 0.165.

* * * * *